United States Patent
Liang et al.

(10) Patent No.: US 10,610,203 B2
(45) Date of Patent: Apr. 7, 2020

(54) METHODS, SYSTEMS, AND MEDIA FOR DETERMINING CAROTID INTIMA-MEDIA THICKNESS

(75) Inventors: Jianming Liang, Phoenix, AZ (US); Xiangjun Zhu, Tempe, AZ (US); Christopher B. Kendall, Scottsdale, AZ (US); Robert T. Hurst, Scottsdale, AZ (US)

(73) Assignees: The Arizona Board of Regents on Behalf of Arizona State University, Scottsdale, AZ (US); The Mayo Foundation for Medical Education and Research, Rochester, MN (US)

( * ) Notice: Subject to any disclaimer, the term of this patent is extended or adjusted under 35 U.S.C. 154(b) by 1587 days.

(21) Appl. No.: 13/984,800

(22) PCT Filed: Feb. 13, 2012

(86) PCT No.: PCT/US2012/024924
§ 371 (c)(1),
(2), (4) Date: Jan. 8, 2014

(87) PCT Pub. No.: WO2012/109676
PCT Pub. Date: Aug. 16, 2012

(65) Prior Publication Data
US 2014/0135627 A1 May 15, 2014

Related U.S. Application Data

(60) Provisional application No. 61/442,169, filed on Feb. 11, 2011.

(51) Int. Cl.
*A61B 8/00* (2006.01)
*A61B 5/02* (2006.01)
(Continued)

(52) U.S. Cl.
CPC ............ *A61B 8/56* (2013.01); *A61B 5/02007* (2013.01); *A61B 8/085* (2013.01); *A61B 8/0891* (2013.01);
(Continued)

(58) Field of Classification Search
None
See application file for complete search history.

(56) References Cited

U.S. PATENT DOCUMENTS 7,526,101 B2    4/2009  Avidan
7,840,061 B2   11/2010  Porikli et al.
(Continued)

OTHER PUBLICATIONS

Steinman et al Reconstruction of Carotid Bifurcation Hemodynamics and Wall Thickness Using Computational Fluid Dynamics and MRI Magnetic Resonance in Medicine 47:149-159, 2002.*
(Continued)

*Primary Examiner* — Serkan Akar
(74) *Attorney, Agent, or Firm* — Byrne Poh LLP

(57) ABSTRACT

Methods, systems, and media for determining carotid intima-media thickness are provided. In some embodiments, a method for determining carotid intima-media thickness of a carotid artery is provided, the method comprising: receiving a frame from a plurality of images, wherein each of the plurality of images includes a portion of the carotid artery; receiving a user selection of a location with the frame; setting a region of interest, based on the received user selection; detecting a first border and a second border within the region of interest; applying one or more active contour models to the first border and the second border to generate a smoothed first border and a smoothed second border; and calculating the intima-media thickness based at least in part on the smoothed first border and the second smoothed border.

33 Claims, 9 Drawing Sheets

(51) Int. Cl.
 G06T 7/00 (2017.01)
 A61B 8/08 (2006.01)
 G06T 7/62 (2017.01)
 A61B 5/107 (2006.01)

(52) U.S. Cl.
 CPC ............ *A61B 8/461* (2013.01); *A61B 8/463* (2013.01); *A61B 8/465* (2013.01); *A61B 8/469* (2013.01); *A61B 8/5223* (2013.01); *G06T 7/0012* (2013.01); *G06T 7/62* (2017.01); *A61B 5/1075* (2013.01); *A61B 8/486* (2013.01); *G06T 2207/10132* (2013.01); *G06T 2207/20036* (2013.01); *G06T 2207/20104* (2013.01); *G06T 2207/20116* (2013.01); *G06T 2207/30101* (2013.01)

(56) References Cited

U.S. PATENT DOCUMENTS

| | | |
|---|---|---|
| 8,812,431 B2 | 8/2014 | Voigt et al. |
| 2003/0199762 A1 | 10/2003 | Fritz et al. |
| 2004/0208341 A1 | 10/2004 | Zhou et al. |
| 2005/0220336 A1 | 10/2005 | Sabe et al. |
| 2005/0228276 A1 | 10/2005 | He et al. |
| 2006/0074834 A1 | 4/2006 | Dong et al. |
| 2006/0204121 A1 | 9/2006 | Bryll |
| 2007/0280530 A1 | 12/2007 | Fung et al. |
| 2008/0009733 A1 | 1/2008 | Saksena |
| 2008/0027887 A1 | 1/2008 | Barbu et al. |
| 2008/0089571 A1 | 4/2008 | Kurita |
| 2008/0154565 A1 | 6/2008 | Florin et al. |
| 2008/0171939 A1 | 7/2008 | Ishihara |
| 2008/0192887 A1 | 8/2008 | Weese et al. |
| 2008/0194957 A1 | 8/2008 | Hoctor et al. |
| 2008/0205750 A1 | 8/2008 | Porikli et al. |
| 2008/0240532 A1 | 10/2008 | Carneiro et al. |
| 2008/0260230 A1 | 10/2008 | Gotardo et al. |
| 2009/0034816 A1 | 2/2009 | Ghanem et al. |
| 2009/0060307 A1 | 3/2009 | Ghanem et al. |
| 2009/0175515 A1 | 7/2009 | Schummers |
| 2009/0252394 A1 | 10/2009 | Liang et al. |
| 2010/0046815 A1 | 2/2010 | Von Berg et al. |
| 2010/0061601 A1 | 3/2010 | Abramoff et al. |
| 2010/0076517 A1 | 3/2010 | Imran |
| 2010/0098308 A1 | 4/2010 | Lakare et al. |
| 2010/0113930 A1 | 5/2010 | Miyachi |
| 2010/0177944 A1 | 7/2010 | Madabhushi et al. |
| 2010/0202681 A1 | 8/2010 | Haizhou et al. |
| 2010/0266176 A1 | 10/2010 | Masumoto et al. |
| 2011/0191283 A1 | 8/2011 | Voigt et al. |
| 2011/0270089 A1 | 11/2011 | Vezina |
| 2011/0293157 A1 | 12/2011 | Ye et al. |
| 2012/0089545 A1 | 4/2012 | Mei et al. |
| 2012/0106815 A1 | 5/2012 | Yang et al. |
| 2012/0130245 A1* | 5/2012 | Chono ................. A61B 8/0891 600/443 |
| 2012/0274755 A1 | 11/2012 | Sinha et al. |
| 2013/0070997 A1 | 3/2013 | Tajbakhsh et al. |
| 2014/0185887 A1 | 7/2014 | Wu et al. |

OTHER PUBLICATIONS

Office Action dated Jun. 15, 2016 in U.S. Appl. No. 14/376,568.
Office Action dated Jul. 20, 2016 in U.S. Appl. No. 13/984,808.
Notice of Allowance dated Sep. 14, 2015 in U.S. Appl. No. 13/621,837.
Office Action dated Jan. 4, 2016 in U.S. Appl. No. 14/023,380.
Office Action dated Sep. 21, 2015 in U.S. Appl. No. 13/984,808.
Office Action dated Nov. 27, 2015 in U.S. Appl. No. 14/376,568.
Patent Examination Report dated Aug. 26, 2015 in Australian Patent Application No. 2012241419.

Alonso-Martinez, J.L., et al., "Delay and Misdiagnosis in Sub-Massive and Non-Massive Acute Pulmonary Embolism", In European Journal of Internal Medicine, vol. 21, No. 4, Aug. 2010, pp. 278-282.
Araoz, P.A., et al., "Helical CT Pulmonary Angiography Predictors of in-Hospital Morbidity and Mortality in Patients with Acute Pulmonary Embolism", In Journal of Thoracic Imaging, vol. 18, Oct. 2003, pp. 207-216.
Bottiger, B.W., et al., "Inhaled Nitric Oxide Selectively Decreases Pulmonary Artery Pressure and Pulmonary Vascular Resistance following Acute Massive Pulmonary Microembolism in Piglets", In Chest, vol. 110, No. 4, Oct. 1996, pp. 1041-1047.
Collomb, J., et al., "Severity Assessment of Acute Pulmonary Embolism: Evaluation using Helical CT", In European Radiology, vol. 13, No. 7, Feb. 2003, pp. 1508-1514.
Dias-Junior, C.A., "The Effect of Sildenafil on Pulmonary Embolism-Induced Oxidative Stress and Pulmonary Hypertension", In Anesthesia & Analgesia, vol. 101, No. 1, Jul. 2005, pp. 115-120.
Ghaye, B., et al., "Can CT Pulmonary Angiography Allow Assessment of Severity and Prognosis in Patients Presenting with Pulmonary Embolism? What the Radiologist Needs to Know", In RadioGraphics, vol. 26, Jan. 2006, pp. 23-29.
Ghaye, B., et al., "Severe Pulmonary Embolism: Pulmonary Artery Clot Load Scores and Cardiovascular Parameters as Predictors of Mortality", In Radiology, vol. 239, Apr. 2006, pp. 884-891.
Grifoni, S.,"Short-Term Clinical Outcome of Patients with Acute Pulmonary Embolism, Normal Blood Pressure, and Echocardiographic Right Ventricular Dysfunction", In Circulation, vol. 101, No. 24, Jun. 2000, pp. 2817-2822.
Howard, G., et al., "For the ARIC Investigators: Carotid Artery Intimal-Medial Thickness Distribution in General Populations as Evaluated by B-Mode Ultrasound", In Stroke, vol. 24, No. 9, Sep. 1993, pp. 1297-1304.
Hurst, R., et al., "Clinical use of Carotid Intima-Media Thickness: Review of the Literature", In Journal of the American Society of Echocardiography, vol. 20, No. 7,2007, pp. 907-914.
Jardin, F., et al., "Echocardiographic Pattern of Acute Cor Pulmonale", In Chest, vol. 111, No. 1, Jan. 1997, pp. 209-217.
Kass, M., et al., "Snakes: Active Contour Models", In International Journal of Computer Vision, vol. 1, No. 4, Jan. 1988, pp. 321-331.
Levenberg, K., "A Method for the Solution of Certain Non-Linear Problems in Least Squares", In Quarterly Journal of Applied Mathmatics, vol. 2, Jul. 1944, pp. 164-168.
Li, S., et al., "Childhood Cardiovascular Risk Factors and Carotid Vascular Changes in Adulthood: the Bogalusa Heart Study", In the Journal of the American Medical Association (JAMA), vol. 290, No. 17, Nov. 2003, pp. 2271-2276.
Liang, J., et al., "United Snakes", In Medical Image Analysis, vol. 10 No. 2, Apr. 2006, vol. 215-233.
Mansencal, N., "Comparison of Different Echocardiographic Indexes Secondary to Right Ventricular Obstruction in Acute Pulmonary Embolism", In the American Journal of Cardiology, vol. 92, No. 1, Jul. 2003, pp. 116-119.
Marquardt, D.W., "An Algorithm for Least-Squares Estimation of Nonlinear Parameters", In SIAM Journal on Applied Mathematics, vol. 11 No. 2, Jun. 1963, pp. 431-441.
Mastora, I., "Severity of Acute Pulmonary Embolism: Evaluation of a New Spiral CT Angiographic Score in Correlation with Echocardiographic Data", In European Radiology, vol. 13, Jan. 2003, pp. 29-35.
McConnell, M.V., et al., "Regional Right Ventricular Dysfunction detected by Echocardiography in Acute Pulmonary Embolism", In the American Journal of Cardiology, vol. 78 No. 4, Aug. 1996, pp. 469-473.
Office Action dated Jan. 22, 2015 in U.S. Appl. No. 14/376,181.
Office Action dated Jan. 29, 2015 in U.S. Appl. No. 13/621,837.
Ribeiro, A., et al., "Echocardiography Doppler in Pulmonary Embolism: Right Ventricular Dysfunction as a Predictor of Mortality Rate", In American Heart Journal, vol. 134, No. 3, Mar. 1997, pp. 479-487.

(56) References Cited

OTHER PUBLICATIONS

Stein, J., et al., "A Semiautomated Ultrasound Border Detection Program that Facilitates Clinical Measurement of Ultrasound Carotid Intima-Media Thickness", in the Journal of the American Society of Echocardiology, vol. 18, No. 3, Mar. 2005, pp. 244-251.
Stein, J., et al., "Use of Carotid Ultrasound to Identify Subclinical Vascular Disease & Evaluate Cardiovascular Disease Risk: A Consensus Statement from the American Society of Echocardiography Carotid Intima-Media Thickness Task Force", In the Journal of Am. Soc. of Echocardiography, vol. 21, No. 2, Feb. 2008, pp. 93-111.
Stein, J., et al., "Vascular Age: Integrating Carotid Intima-Media Thickness Measurements with Global Coronary Risk Assessment", In Clinical Cardiology, vol. 27, No. 7, Jul. 2004, pp. 388-392.
Tajbakhsh, N., et al., "Motion Analysis of Right Ventricular Dysfunction under Mild and Moderate Pressure Overload caused by Acute Pulmonary Embolism", In Ultrasound in Medicine and Biology, vol. 39, No. 11, Nov. 2013, pp. 2066-2074.
Tajbakhsh, N., et al., "Shape-Based Analysis of Right Ventricular Dysfunction associated with Acute Pulmonary Embolism", In SPIE Medical Imaging, vol. 8317, Mar. 2012, pp. 1-5.
Takamura, T., et al., "Reversible Left Ventricular Regional Non-Uniformity Quantified by Speckle-Tracking Displacement and Strain Imaging in Patients with Acute Pulmonary Embolism", In Journal of the American Society of Echocardiography, vol. 24, No. 7, Apr. 2011, pp. 792-802.
Wu, H., "Offline and Online Adaboost for Detecting Anatomical Structures", Thesis Paper, Arizona State University, Aug. 2011, pp. 1-66.
Wu, H., et al. "Self-Adaptive Asymmetric on-line Boosting for Detecting Anatomical Structures", In SPIE Medical Imaging, vol. 8315, Feb. 2012, pp. 1-7.
"Deep Vein Thrombosis Overview", Technical Report, Society of Interventional Radiology, last accessed Sep. 17, 2014, pp. 1-3, available at: http://www.sirweb.org/patients/deep-vein-thrombosis/.
Bi, J. and Liang, J., "Multiple instance learning of pulmonary embolism detection with geodesic distance along vascular structure", In Proceedings of IEEE Computer Society Conference on Computer Vision and Pattern Recognition (CVPR) Jun. 17-22, 2007, Minneapolis, MN, USA, pp. 1-8.
Bouma, H., "Vessel-Diameter Quantification and Embolus Detection in CTA Images." Ph.D. Thesis, Eindhoven University of Technology, PrintPartners, Ipskamp, The Netherlands, Apr. 2008, pp. 9-133.
Bouma, H., et al, "Automatic Detection of Pulmonary Embolism in CTA Images", In IEEE Transactions on Medical Imaging, vol. 28, No. 8, Aug. 2009, pp. 1223-1230.
Bourdev, L. and Brandt, J., et al., "Robust Object Detection via Soft Cascade", In Proceedings of the 2005 IEEE Conference on Computer Vision and Pattern Recognition (CVPR '05), Washington, DC, USA, Jun. 2005, pp. 236-243.
Chartrand-Lefebvre, C., "Computed tomography angiography in the diagnosis of pulmonary embolism: Interobserver agreement", In American Journal of Emergency Medicine, Jan. 27, 2011, pp. 118-119.
Cho, E.J., et al., "Right ventricular free wall circumferential strain reflects graded elevation in acute right ventricular afterload", In Am J Physiol Heart Circ Physiol., Feb. 2009, vol. 296, No. 2, pp. 818-824.
Costantino, G., et al., "Interobserver agreement in computer tomography readings for pulmonary embolism", In American Journal of Emergency Medicine, Jan. 27, 2011, pp. 119.
Costantino, G., et al., "Interobserver agreement in computer tomography readings for pulmonary embolism", In American Journal of Emergency Medicine, vol. 27, No. 9, Nov. 2009, pp. 1109-1111.
Craig, J.J., "Introduction to Robotics: Mechanics and Control", 3rd edition, Prentice Hall, Aug. 6, 2004, pp. 1-385.
Criminisi, A., et al., "Regression Forests for Efficient Anatomy Detection and Localization in CT Studies", In Proceedings of the International Workshop on Medical Computer Vision, Beijing, CN, Sep. 2010, pp. 106-117.
Crow, F.C., "Summed-Area Tables for Texture Mapping", In Computer Graphics, vol. 18, No. 3, Jul. 1984, pp. 207-212.
Dinesh, M.S., et al, "Adaptive Contrast-Based Computer Aided Detection for Pulmonary Embolism", In Proceedings of the SPIE International Society Conference for Optimal Engineering, Mar. 2009, vol. 7260, No. 726010, pp. 1-8.
Dollar, P., et al., "Multiple Component Learning for Object Detection", In Proceedings of the 10th European Conference on Computer Vision: Part II (ECCV '08), Marseille, FR, Oct. 12-18, 2008, pp. 211-224.
Dousset, M., et al., "Principles and performance of virtual CT and MIRA intraluminal endoscopy", In Virtual Endoscopy, Springer, Nov. 2002, pp. 1-19.
Frangi, A.F., et al., "Multiscale vessel enhancement filtering", In Medical Image Computing and Computer-Assisted Intervention, Oct. 11-13, 1998, pp. 130-137.
Freund, Y. and Schapire, R.E., "A Decision-Theoretic Generalization of on-Line Learning and an Application to Boosting", In Journal of Computer and System Sciences, vol. 55, No. 1, Aug. 1997, pp. 119-139.
Freund, Y. and Schapire, R.E., "A Short Introduction to Boosting", In Journal of Japanese Society for Artificial Intelligence, vol. 14, No. 5, Sep. 1999, pp. 771-780.
Galson, S.K., "The surgeon general's call to action to prevent deep vein thrombosis and pulmonary embolism", Technical Report, U.S. Public Health Services, Sep. 15, 2008, pp. 1-35.
Godec, M., et al., "On-line Random Naive Bayes for Tracking", In Proceedings of the 20th International Conference (ICPR '10), Istanbul, TR, Aug. 23-26, 2010, pp. 3545-3548.
Goldstein, H., "Classical Mechanics", 2nd Edition, Jul. 1980, pp. 1-2.
Grabner, H. and Bischof, H., "On-line Boosting and Vision", In Proceedings of the IEEE Computer Society Conference on Computer Vision and Pattern Recognition (CVPR '06), New York, NY, USA, Jun. 17-22, 2006, pp. 260-267.
Grbovic, M. and Vucetic, S., "Tracking Concept Change with Incremental Boosting by Minimization of the Evolving Exponential Loss", In Proceedings of the European Conference on Machine Learning and Knowledge Discovery in Databases, Athens, GR, Sep. 5-9, 2011, pp. 516-532.
Groth, M., et al., "Correlation of right ventricular dysfunction parameters and pulmonary vascular obstruction score in acute pulmonary embolism in a porcine model", In Emergency Radiology, Sep. 2010, pp. 367-374.
He, H., et al., "Incremental Learning from Stream Data," In IEEE Transactions on Neural Networks, vol. 22, No. 12, Dec. 2011, pp. 1901-1914.
International Patent Application No. PCT/US2013/024675, filed Feb. 4, 2013.
International Patent Application No. PCT/US2013/024677, filed Feb. 4, 2013.
International Preliminary Report on Patentability dated Aug. 22, 2013 in International Patent Application No. PCT/US2012/024925.
International Preliminary Report on Patentability in International Application No. PCT/US2012/024907, filed Feb. 13, 2012, dated Aug. 22, 2013.
International Search Report in International Patent Application No. PCT/US2012/024925, filed Feb. 13, 2012, dated Jun. 19, 2012.
International Search Report in International Patent Application No. PCT/US2013/024675, filed Feb. 4, 2013, dated Apr. 16, 2013.
International Search Report in International Patent Application No. PCT/US2013/024677, filed Feb. 4, 2013, dated Apr. 15, 2013.
Kanitsar, A., et al., "CPR—Curved Planar Reformation", In Proceedings of IEEE Visualization, Nov. 1, 2002, pp. 37-44.
Kim, T.K., et al., "Online Multiple Classier Boosting for Object Tracking", In Proceedings of the 2010 IEEE Computer Society Conference on Computer vision and Pattern Recognition Workshops (CVPRW '10), San Francisco, CA, USA, Jun. 13-18, 2010, pp. 1-6.
Kiraly, A.P., et al., "Cartwheel projections of segmented pulmonary vasculature for the detection of pulmonary embolism", In Medical Imaging: Visualization, Image-Guided Procedures, and Display, Proc. SPIE 5744, Apr. 12, 2005, pp. 69-78.

(56) References Cited

OTHER PUBLICATIONS

Knutsson, H., "Representing Local Structure using Tensors", In Proceedings of the 6th Scandinavian Conference on Image Analysis, Oulu, Finland, Jun. 1989, pp. 244-251.

Kothe, U., "Edge and Junction Detection with an Improved Structure Tensor", In Proceedings of the 25th DAGM Symposium on Pattern Recognition, Magdeburg, DE, Sep. 10-12, 2003, pp. 25-32.

Kurkure, U., et al., "Automated Segmentation of Thoracic Aorta in Non-Contrast CT Images", In Proceedings of the 5th International Symposium on Biomedical Imaging: From Nano to Macro (ISBI '08), Paris, FR, May 14-17, 2008, pp. 29-32.

Leistner, C., et al., "On Robustness of on-Line Boosting—A Competitive Study", In Proceedings of the 2009 IEEE 12th International Conference on Computer Vision Workshops (ICCVW '09), Kyoto, JP, Sep. 27-Oct. 4, 2009, pp. 1362-1369.

Liang, J. and Bi, J., "Computer Aided Detection of Pulmonary Embolism with Tobogganing and Multiple Instance Classification in CT Pulmonary Angiography", In Proceedings of the 20th Intl Conference of Information Processing in Medical Imaging Kerkrade, NL, Jul. 2-6, 2007, pp. 630-641.

Liang, J. and Bi, J., "Local Characteristic Features for Computer-Aided Detection of Pulmonary Embolism in CT Angiography", In Proceedings of the First Workshop on Pulmonary Image Analysis, New York, NY, US, Sep. 6, 2008, pp. 263-272.

Liu, D., et al., "Search strategies for multiple landmark detection by submodular maximization", IEEE Conference on Computer Vision and Pattern Recognition, Jun. 3-8, 2010, San Francisco, CA, USA, pp. 2831-2838.

Liu, X. and Yu, T., "Gradient Feature Selection for Online Boosting", In Proceedings of the IEEE 11th International Conference on Computer Vision (ICCV '07), Rio de Janeiro, BR, Oct. 14-21, 2007, pp. 1-8.

Lorenz, C., et al., "Multi-scale line segmentation with automatic estimation of width, contrast and tangential direction in 2-D and 3-D medical images", In Proc. of the Joint Conference on Computer Vision, Virtual Reality and Robotics in Medicine, London, UK, Mar. 19-22, 1997, pp. 233-242.

Masutani, Y., et al., "Computerized Detection of Pulmonary Embolism in Spiral CT Angiography Based on Volumetric Image Analysis", In IEEE Transactions on Medical Imaging, vol. 21, No. 12, Dec. 2002, pp. 1517-1523.

Office Action dated Jul. 17, 2014 in U.S. Appl. No. 13/621,837.
Office Action dated Aug. 23, 2013 in U.S. Appl. No. 13/984,808.
Office Action dated Oct. 7, 2013 in U.S. Appl. No. 14/023,380.
Office Action dated Sep. 18, 2013 in European Patent Application No. 12744949.4.

Ouellette, D.R., et al., "Pulmonary Embolism", Medscape.com, last updated Sep. 4, 2014, available at: http://emedicine.medscape.com/article/300901-overview#showall, pp. 1-24.

Oza, N. C. and Russell, S., "Online Bagging and Boosting", In Artificial Intelligence and Statistics, 2001, pp. 105-112.

Parag, T., et al., "Boosting Adaptive Linear Weak Classifiers for Online Learning and Tracking", In Proceedings of the IEEE Conference on Computer Vision and Recognition (CVPR '08), Anchorage, AK, USA, Jun. 23-28, 2008, pp. 1-8.

Parikh, D. and Polikar, R., "An Ensemble-Based Incremental Learning Approach to Data Fusion", In IEEE Transactions on Systems, Man, Cybernetics, Part B: Cybernetics, vol. 37, No. 2, Apr. 2007, pp. 437-450.

Pelossof, R., et al., "Online Coordinate Boosting", In Proceedings of the 2009 IEEE 12th International Conference on Computer Vision Workshops, (ICCVW '09), Kyoto, JP, Sep. 27-Oct. 4, 2009, pp. 1354-1361.

Pham, M. and Cham, T., "Detection with Multi-exit Asymmetric Boosting", In Proceedings of the IEEE Conference on Computer Vision and Pattern Recognition (CVPR '08), Anchorage, AK, USA, Jun. 23-28, 2008, pp. 1-8.

Pham, M. and Cham, T., "Fast Training and Selection of Haar Features Using Statistics in Boosting-Based Face Detection", In Proceedings of the IEEE 11th International Conference on Computer Vision (ICCV '07), Rio de Janeiro, BR, Oct. 14-21, 2007, pp. 1-7.

Pham, M. and Cham, T., "Online Learning Asymmetric Boosted Classifiers for Object Detection", In Proceedings of the IEEE Conference on Computer Vision and Recognition (CVPR '07), Minneapolis, MN, USA, Jun. 17-22, 2007, pp. 1-8.

Sato, Y. et al., "3-D multi-scale line filter for segmentation and visualization of curvilinear structures in medical images", In Proc. of the Joint Conference on Computer Vision, Virtual Reality and Robotics in Medicine, London, UK, Mar. 19-22, 1997, pp. 213-222.

Schapire, R. E. and Singer, Y., "BoosTexter: A Boosting-Based System for Text Categorization", In Machine Learning, vol. 39, No. 2, May 1, 2000, pp. 135-168.

Schapire, R. E., "Theoretical Views of Boosting and Applications", In Algorithmic Learning Theory, Lecture Notes in Computer Science, vol. 1720, Dec. 1999, pp. 13-25.

Sebbe, R., "Computer-aided Diagnosis of Pulmonary Embolism in Opacified CT Images", Ph.D. Dissertation, Faculte Polytechnique de Mons, Universitaires de Louvain, Belgium, Feb. 20, 2007, pp. 1-124.

Simon, M., et al., "Paddle-wheel CT display of pulmonary arteries and other lung structures: a new imaging approach", In American Journal of Roentgenology, Jul. 2001, pp. 195-198.

Simon, M., et al., "Paddle-wheel multislice helical CT display of pulmonary vessels and other lung structures", In Radiologic Clinics of North America, May 2003, pp. 617-626.

Stein, P.D. and Hull, R.D., "Multidetector computed tomography for the diagnosis of acute pulmonary embolism", In Current Opinion Pulmonary Medicine, Sep. 2007, pp. 384-388.

Stein, P.D. and Matta, F., "Acute Pulmonary Embolism", In Current Problems in Cardiology, vol. 35, No. 7, Jul. 2010, pp. 314-376.

Sternig, S., et al., "Transient Boost: On-line Boosting with Transient data", In Proceedings of the 2010 IEEE Computer Society Conference on Computer Vision and Pattern Recognition Workshops (CVPRW '10), San Francisco, CA, USA, Jun. 13-18, 2010, pp. 22-27.

Torbicki, A., et al., "Guidelines on the diagnosis and management of acute pulmonary embolism of the European Society of Cardiology", In Eur Heart J., vol. 29, No. 18, Sep. 2008, pp. 2276-2315.

Vaidehi, V., et al., "Multiclass Object Detection System in Imaging Sensor Network Using Haar-like Features and Joint-Boosting Algorithm", In Proceedings of the 2011 International Conference on Recent Trends in Information Technology (ICRTIT '11), Chennai, Tamil Nadu, IN, Jun. 3-5, 2011, pp. 1011-1015.

Viola, P. and Jones M., "Fast and Robust Classification Using Asymmetric AdaBoost and a Detector Cascade", In Proceedings of the Annual Conference on Neural Information Processing Systems, Vancouver, BC, CA, Dec. 3-8, 2001, pp. 1311-1318.

Viola, P. and Jones, M., "Rapid Object Detection using a Boosted Cascade of Simple Features", In Proceedings of the IEEE Computer Society Conference on Computer Vision and Pattern Recognition, Kauai, HI, USA. Dec. 8-14, 2001, pp. 511-518.

Written Opinion in International Patent Application No. PCT/US2012/024925, filed Feb. 13, 2012, dated Jun. 19, 2012.
Written Opinion in International Patent Application No. PCT/US2013/024675, filed Feb. 4, 2013, dated Apr. 16, 2013.
Written Opinion in International Patent Application No. PCT/US2013/024677, filed Feb. 4, 2013, dated Apr. 15, 2013.

Wu, B. and Nevatia, R., "Improving Part Based Object Detection by Unsupervised, Online Boosting", In Proceedings of the IEEE Conference on Computer Vision and Pattern Recognition (CVPR '07), Minneapolis, MN, USA, Jun. 17-22, 2007, pp. 1-8.

Wu, H., et al., "Machine Learning based Automatic Detection of Pulmonary Trunk", In Proceedings of the SPIE Conference on Medical Imaging 2011: Computer-Aided Diagnosis, Lake Buena Vista, FL, USA, Feb. 12, 2011, vol. 7963, pp. 1-6.

Zheng, Y., et al., "Automatic Aorta Segmentation and Valve Landmark Detection in C-Arm CT: Application to Aortic Valve Implantation", In IEEE Transactions on Medical Imaging, vol. 31, No. 12, Dec. 2012, pp. 2307-2321.

(56) References Cited

OTHER PUBLICATIONS

Zheng, Y., et al., "Fast Automatic Heart Chamber Segmentation from 3D CT Data Using Marginal Space Learning and Steerable Features", In Proceedings of the IEEE 11th International Conference on Computer Vision (ICCV '07), Rio de Janeiro, BR, Oct. 14-21, 2007, pp. 1-8.

Zhou, C., et al., "Automatic Pulmonary Vessel Segmentation in 3D Computed Tomographic Pulmonary Angiographic (CTPA) Images", In Proceedings of the SPIE 6144, Medical Imaging: Image Processing, Mar. 15, 2006, pp. Q1-Q7.

Zhou, S. K., et al., "A Boosting Regression Approach to Medical Anatomy Detection", In Proceedings of the IEEE Conference on Computer Vision and Pattern Recognition (CVPR '07), Minneapolis, MN, USA, Jun. 17-22, 2007, pp. 1-8.

Zou, X., et al., "Anatomy-Based Automatic Detection and Segmentation of Major Vessels in Thoracic CTA Images", In Computerized Medical Imaging and Graphics, vol. 30, No. 5, Jul. 2006, pp. 299-313.

Frangi, A.F., et al., "Model-Based Quantitation of 3-D Magnetic Resonance Angiographic Images", In IEEE Transactions on Medical Imaging, vol. 18, No. 10, Oct. 1999, pp. 946-956.

Office Action dated Apr. 24, 2015 in U.S. Appl. No. 14/023,380.

\* cited by examiner

METHODS, SYSTEMS, AND MEDIA FOR DETERMINING CAROTID INTIMA-MEDIA THICKNESS

CROSS REFERENCE TO RELATED APPLICATIONS

This application claims the benefit of U.S. Provisional Patent Application No. 61/442,169, filed Feb. 11, 2011, which is hereby incorporated by reference herein in its entirety.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

The disclosed subject matter relates to methods, systems, and media for determining carotid intima-media thickness. More particularly, the disclosed subject matter relates to determining carotid intima-media thickness, where active contour models can be used to detect inner borders of the carotid artery.

BACKGROUND

Given the high morbidity, mortality, and the large societal burden associated with cardiovascular diseases, there are numerous approaches for assessing cardiovascular health. One of these approaches determines whether a patient has atherosclerosis by measuring carotid intima-media thickness (CIMT). Atherosclerosis is a condition where fat, cholesterol, and other substances build up in the walls of arteries and form hard structures called plaques. Over time, these plaques can block arteries and cause symptoms and problems through the body, such as aneurysms, plaque ruptures, blood clots, heart attacks, and strokes. Current studies have shown that carotid intima-media thickness can be used as an independent predictor of future mortality, myocardial infarction, and stroke risk.

The carotid intima-media thickness (CIMT) can be measured using B-mode ultrasound sonography. Such measurement provides a non-invasive, sensitive, and highly reproducible technique for cardiovascular risk stratification. However, measuring the carotid intima-media thickness with B-mode ultrasound sonography requires a precise measurement of the thickness of the intimal and medial layers of the carotid artery that can be tedious, time consuming, and demands specialized expertise and experience. For example, a sonographer uses a high-resolution B-mode ultrasound transducer to obtain image data of the carotid artery. The sonographer then manually draws a region of interest in the obtained image data that includes the walls of the carotid artery. Using this image data, the sonographer can determine the carotid intima-media thickness by measuring the distance between the lumen-intima interface and the media-adventitia interface. Performing this measurement requires significant time for interpreting the image data and considerable experience to achieve accurate and reproducible measurements using current approaches. This is particularly troublesome with the high demand and increasing volume of CIMT examinations.

Accordingly, it is desirable to provide methods, systems, and media for determining carotid intima-media thickness that overcome these and other deficiencies of the prior art.

SUMMARY

Mechanisms for determining carotid intima-media thickness are provided.

These mechanisms include, for example, receiving one or more ultrasound images of a carotid artery and setting a region of interest in an ultrasound image that contains a portion of the carotid artery. These mechanisms can then use active contour models to detect the lumen-intima interface and the media-adventitia interface of the carotid artery within the region of interest. This allows users to accurately and/or adaptively detect the lumen-intima interface and the media-adventitia interface of the carotid artery within the region of interest.

Upon detecting the lumen-intima interface and the media-adventitia interface of the carotid artery within the region of interest, the mechanisms can calculate, among other things, the mean carotid intima-media thickness, the maximum carotid intima-media thickness, and the vascular age of a carotid artery.

It should be noted that these mechanisms can be used in a variety of applications. For example, these mechanisms can be used in a clinical environment to interpret image data received from an ultrasound imaging device. In another example, these mechanisms can be used by novice readers to perform various measurements and interpret image data received from an imaging device. In yet another example, these mechanisms can be used by medical professional to alert the professional that a patient has atherosclerosis based on the measured carotid intima-media thickness.

In accordance with various embodiments of the disclosed subject matter, a method for determining carotid intima-media thickness of a carotid artery is provided. The method comprises: receiving a frame from a plurality of images, wherein each of the plurality of images includes a portion of the carotid artery; receiving a user selection of a location with the frame; setting a region of interest based on the received user selection; detecting a first border and a second border within the region of interest; applying one or more active contour models to the first border and the second border to generate a smoothed first border and a smoothed second border; and calculating the intima-media thickness based at least in part on the smoothed first border and the second smoothed border.

In some embodiments, the method further comprises receiving a hard constraint on at least one of the smoothed first border and the smoothed second border, wherein the one or more active contour models are applied such that the smoothed first border or the smoothed second border are directed through the hard constraint.

In some embodiments, the method further comprises automatically updating the smoothed first border or the second smoothed border in response to modifying the hard constraint. In some embodiments, the method further comprises automatically updating the smoothed first border or the second smoothed border using the one or more active contour models in response to receiving a plurality of hard constraints.

In some embodiments, the region of interest includes a plurality of horizontal pixels. In some embodiments, for calculating the intima-media thickness, the method further comprises determining a plurality of carotid intima-media length values, where each of the plurality of carotid intima-media length values is a length of a line orthogonal from the smoothed first border to the smoothed second border for each horizontal pixel within the region of interest.

In some embodiments, the method comprises determining at least one of: a mean carotid intima-media thickness from the plurality of carotid intima-media length values, a maximum carotid intima-media thickness from the plurality of carotid intima-media length values, and a mean of the maximum carotid intima-media thickness from the plurality of carotid intima-media length values over a plurality of regions of interest along the carotid artery.

In some embodiments, the method comprises transmitting the carotid intima-media thickness to a database that relates age to carotid intima-media thickness values. A vascular age corresponding to the carotid artery can then be received from the database.

In some embodiments, the method comprises initializing the one or more active contour models by automatically detecting a first rough border and a second rough border within the region of interest and providing the first rough border and the second rough border to the one or more active contour models.

In some embodiments, the method comprises further simultaneously displaying the first smoothed border, the second smoothed border, and an orthogonal line connecting the first smoothed border and the second smoothed border identifying a location of a maximum carotid intima-media thickness, wherein a color indicator is assigned to each of the first smoothed border and the second smoothed border to indicate the detected borders.

In some embodiments, the method comprises assigning a color indicator to a portion of the carotid artery within the region of interest to indicate a range of the carotid intima-media thickness for the portion.

In accordance with some embodiments, a system for determining carotid intima-media thickness of a carotid artery is provided, the system comprising: an ultrasound imaging device that captures a plurality of ultrasound images, wherein each of the plurality of ultrasound images includes a portion of the carotid artery; and a processor connected to the ultrasound imaging device. The processor is configured to: receive a frame from a plurality of images; receive a user selection of a location with the frame; set a region of interest based on the received user selection; detect a first border and a second border within the region of interest; apply one or more active contour models to the first border and the second border to generate a smoothed first border and a smoothed second border; and calculate the intima-media thickness based at least in part on the smoothed first border and the second smoothed border.

In accordance with some embodiments, a non-transitory computer-readable medium containing computer-executable instructions that, when executed by a processor, cause the processor to perform a method for determining carotid intima-media thickness is provided, the method comprising: receiving a frame from a plurality of images, wherein each of the plurality of images includes a portion of the carotid artery; receiving a user selection of a location with the frame; setting a region of interest based on the received user selection; detecting a first border and a second border within the region of interest; applying one or more active contour models to the first border and the second border to generate a smoothed first border and a smoothed second border; and calculating the intima-media thickness based at least in part on the smoothed first border and the second smoothed border.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION

In accordance with some embodiments of the disclosed subject matter, an image interpretation application for determining carotid intima-media thickness (sometimes referred to herein as "the application") is provided. The image interpretation application can receive an ultrasound image of a carotid artery, set a region of interest in the ultrasound image that contains a portion of the carotid artery, and detect the borders of the carotid artery. Active contour models or snake models and, in some embodiments, user-inputted constraints, can then be applied to the detected borders. The image interpretation application provides users with an accurate, adaptive, and user-friendly approach for detecting borders of the carotid artery.

Using these detected borders, the image interpretation application can perform a variety of measurements. For example, the image interpretation application can determine the carotid intima-media thickness. In another example, the image interpretation application can determine the vascular age of a carotid artery.

Figure 1:
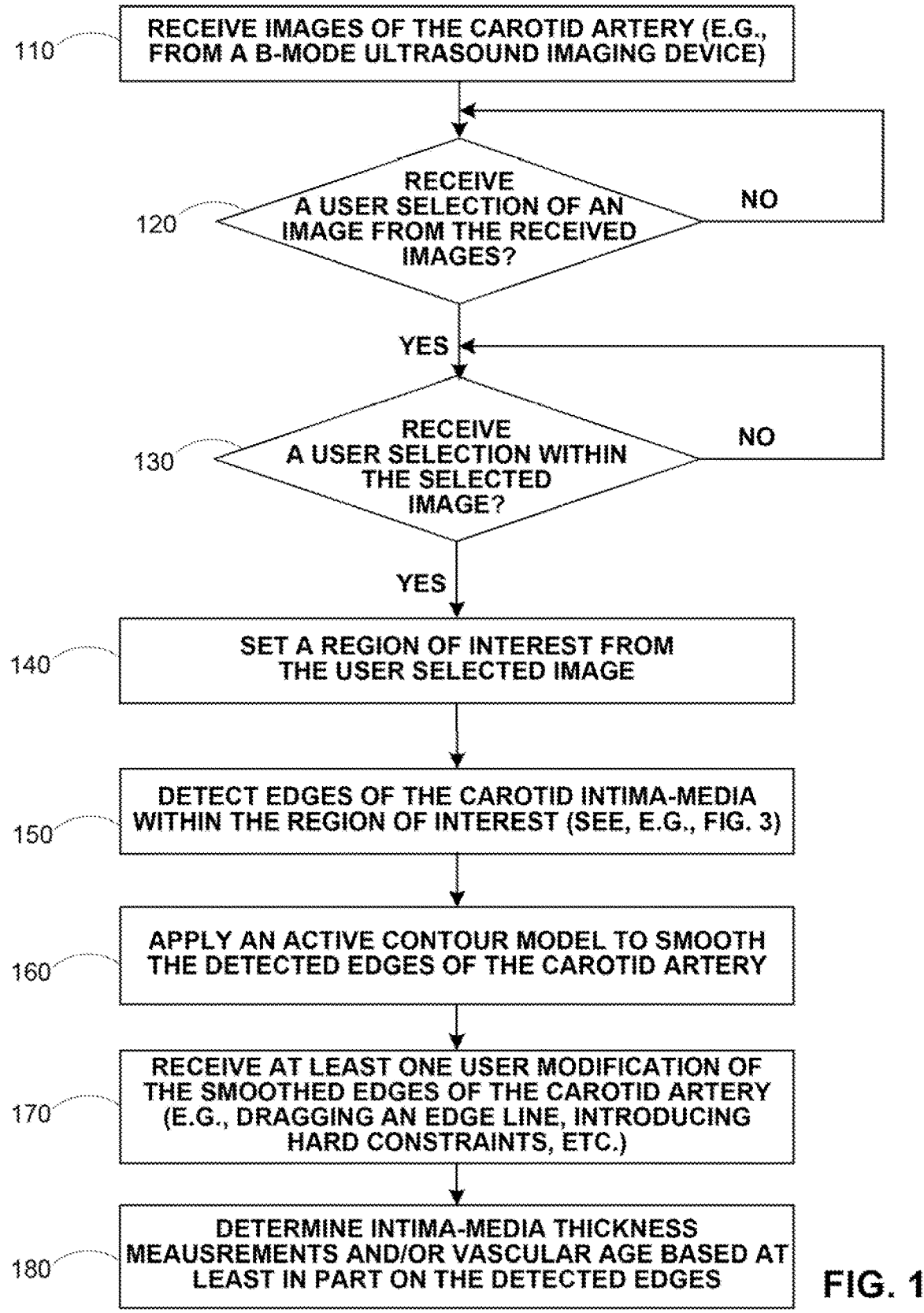
FIG. 1 is an illustrative example of a process for determining carotid intima-media thickness and other suitable measurements using active contour models in accordance with some embodiments of the disclosed subject matter.

Turning to FIG. 1, FIG. 1 shows an illustrative flow diagram 100 for detecting carotid intima-media thickness and other suitable measurements using active contour models in accordance with some embodiments of the disclosed subject matter.

At 110, the image interpretation application can receive multiple images of the carotid artery from an ultrasound imaging device. The ultrasound imaging device can be connected to a processor that is executing the image interpretation application. For example, the carotid artery of a patient can be imaged using a high resolution B-mode ultrasound imaging device with an 8-14 MHz linear array transducer utilizing fundamental frequency. The transducer transmits ultrasound signals into a portion of the patient underneath the transducer and receives echo signals reflected from that portion. In a more particular example, a carotid artery plaque screen can be performed in the transverse and longitudinal axis, revealing the common carotid artery (CCA), the carotid bulb, the carotid bifurcation, and the internal and external carotid arteries. After obtaining longitudinal two-dimensional images of the distal common carotid artery, far wall lumen-intima and media-adventitia interface at the level of the common carotid artery can be adjusted by modifying overall gain, time gain compensation, and focus position.

In some embodiments, the image interpretation application can cause the received images to be displayed to the user. For example, the image interpretation application can access a storage location to retrieve the multiple images for display. In another example, the image interpretation application can update and display the multiple images as the images are being captured using the ultrasound imaging device. In yet another example, the image interpretation application can receive the multiple images of the carotid artery in response to establishing a connection with the ultrasound imaging device (e.g., a wired connection or a wireless connection). More particularly, in some embodiments, the ultrasound imaging device can transmit the images to the image interpretation application.

Figure 2:
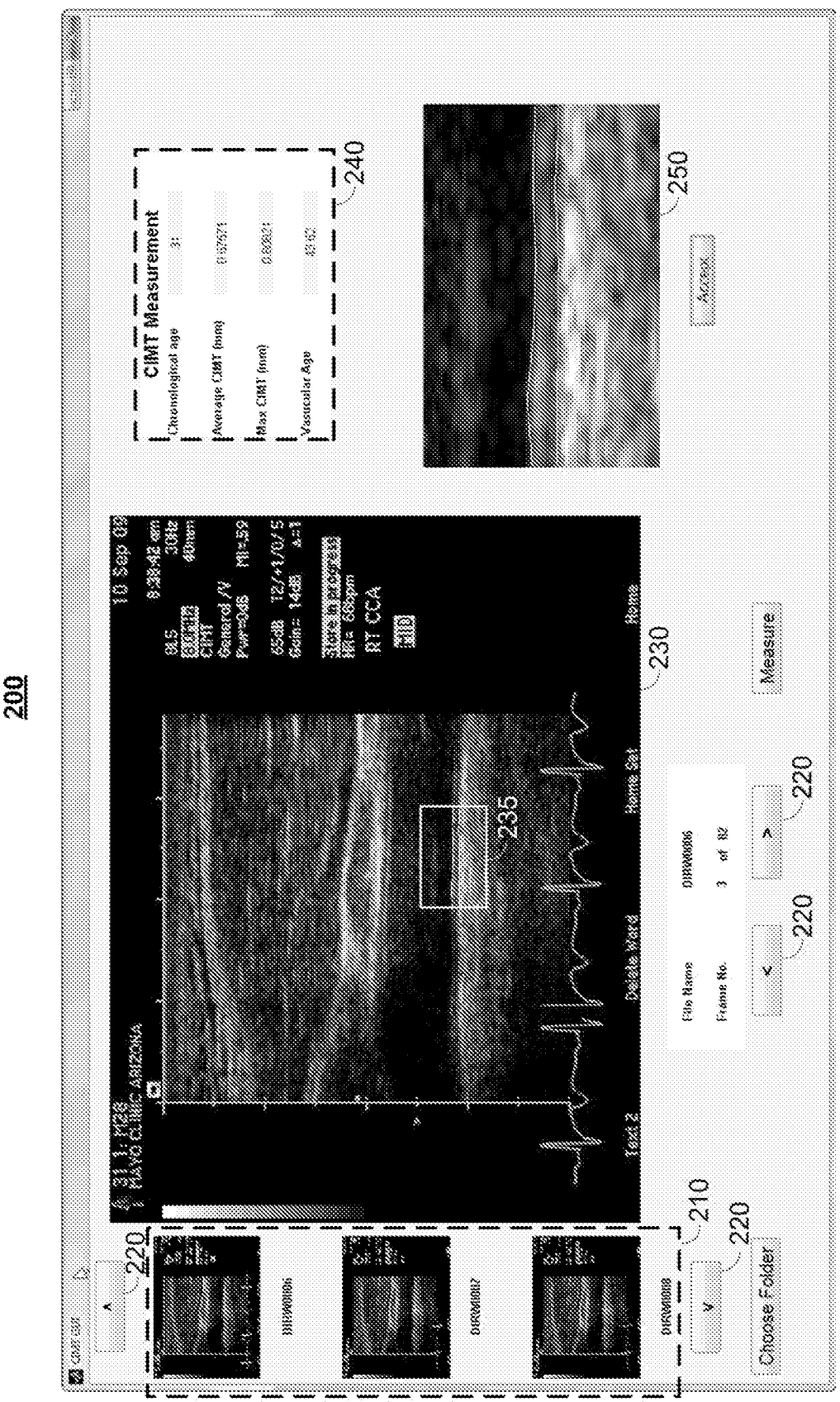
FIG. 2 is an illustrative display screen for selecting an image from a sequence of acquired ultrasound images of a carotid artery and determining the carotid intima-media thickness and other measurements in accordance with some embodiments of the disclosed subject matter.

From the received images, the image interpretation application can receive a user selection of an image or a frame at 120. For example, as shown in display screen 200 of FIG. 2, the image interpretation application presents the user with display screen 200 that includes multiple ultrasound images 210 (e.g., each image is labeled by a file name, such as DIRW0006, DIRW0007, and DIRW0008). Display screen 200 shows that additional images can be displayed in response to the user selecting one of the navigational icons 220. (Pressing an arrow key on a user input device may affect display screen 200 in a similar manner as selecting navigational icon 220.) As also shown in FIG. 2, the user has selected or identified a single, end-diastolic still frame for intima-media measurement analysis (which is indicated as frame number 3 out of 82 frames or images). In response to receiving a user selection of an image at 120, the image interpretation application can cause the selected image to be displayed in image window 230.

Referring back to FIG. 1, the image interpretation application can receive a user selection of a point within the selected image at 130. For example, a user using a user input device (e.g., a mouse, a trackball, a keyboard, etc.) can navigate a cursor or pointer to a location within the selected image and select that location. In response to receiving the user selection at 130, the image interpretation application can set a region of interest within the user-selected image at 140. As shown in FIG. 2, in response to receiving a mouse click on image 230, the image interpretation application sets a region of interest 235 within image 230 for detecting the borders of the carotid artery and calculating carotid intima-media thickness measurements and vascular age. In this particular example, the region of interest 235 is about one centimeter in length and about 0.65 centimeters in height. However, it should be noted that any suitable region of interest can be provided by the image interpretation application.

It should also be noted that, in some embodiments, the user selection of a portion of the ultrasound image is the only user selection received prior to automatically measuring the carotid intima-media thickness from the image. For example, in response to receiving a user selection within the image, the image interpretation application can automatically set a region of interest, detect edge lines or other image information from the region of interest (e.g., initialize by detecting rough edges and smooth those rough edges with one or more active contour models), and calculate a number of parameters, such as a mean carotid intima-media thickness value, a maximum carotid intima-media thickness value, a mean of the maximum carotid intima-media thickness values, and/or a vascular age. As illustrated in region 240 of FIG. 2, in response to receiving the user selection within still frame number 3, the image interpretation application places the region of interest 235, detects the edge lines corresponding to the lumen-intima interface and the media-adventitia interface, and determines that the carotid artery in the selected image has a mean carotid intima-media thickness of 0.67571 millimeters, a maximum carotid intima-media thickness of 0.80821 millimeters, and a vascular age of 43.62.

Additionally or alternatively, the image interpretation application can provide the user with the opportunity to modify or adjust the region of interest. For example, the image interpretation application can allow the user to move the region of interest to a different area within the ultrasound image. In another example, the image interpretation application can allow the user to change the dimensions of the region of interest (e.g., the height, the length, the aspect ratio, etc.). In yet another example, the image interpretation application can allow the user to modify the shape of the region of interest (e.g., from a rectangular region of interest to a circular region of interest).

Upon setting the region of interest, the image interpretation application can detect the edges or borders of the carotid artery within the region of interest at 150. In some embodiments, the image interpretation application begins by obtaining rough or preliminary borders of the carotid artery. That is, the image interpretation application performs an initialization that includes obtaining rough or preliminary borders of the carotid artery. Instead of receiving an initial curve or shape drawn or inputted by a user, such as a medical professional, the image interpretation application performs an accurate initialization that includes a preliminary detection of the borders of the carotid artery within the region of interest.

Figure 3:
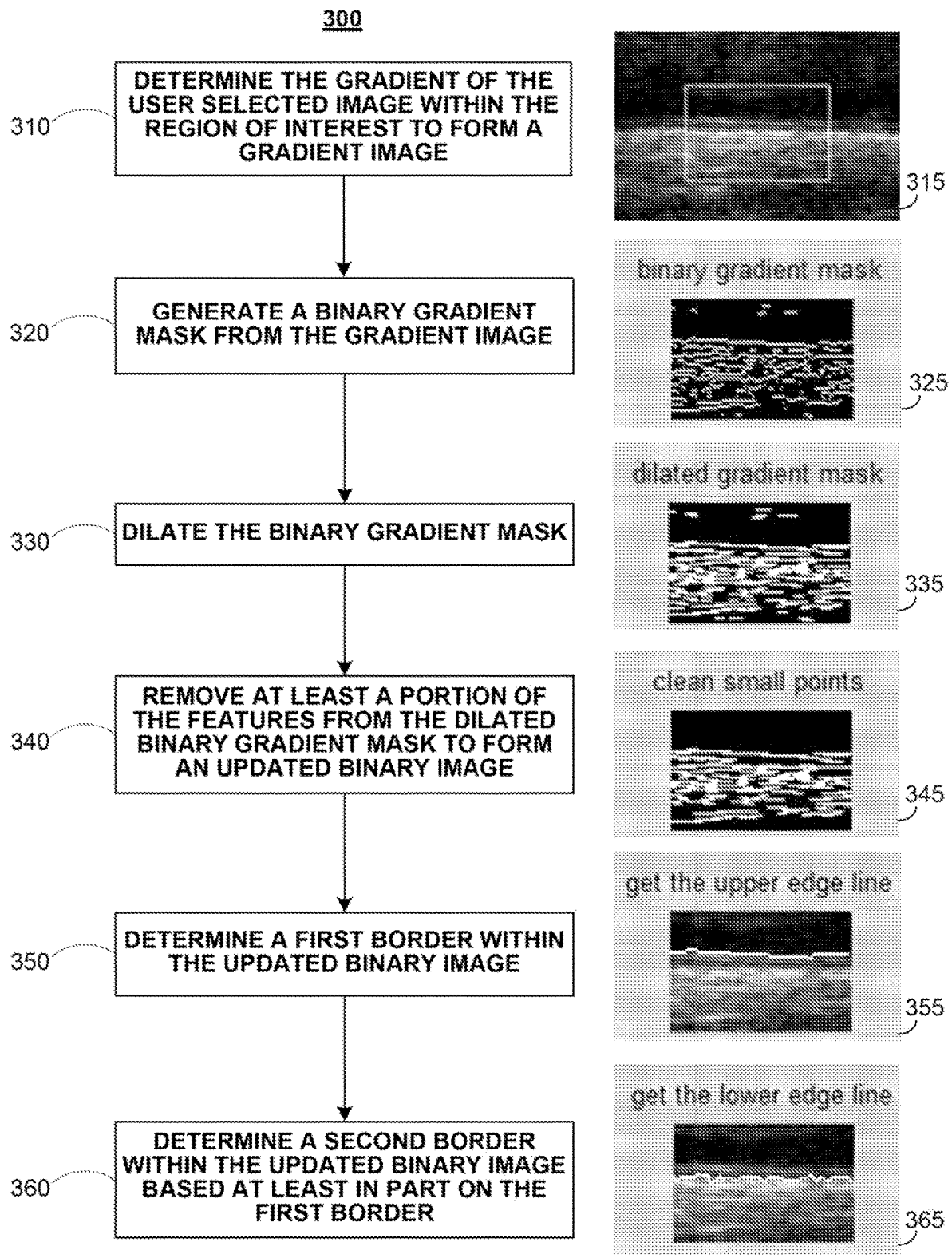
FIG. 3 is an illustrative example of a process for detecting the edges of the carotid artery (the lumen-intima interface and the media-adventitia interface) along with illustrative images with the application of various tools to detect the edges of the carotid artery in accordance with some embodiments of the disclosed subject matter.

FIG. 3 shows an illustrative flow diagram 300 for detecting preliminary borders within a region of interest in accordance with some embodiments of the disclosed subject matter. At 310, the image interpretation application begins by calculating the gradient of the image at each point of the user selected image within the region of interest 315 to form a gradient image. The determination of the gradient of the image can provide, for example, an indication of the change in the intensity or color in the image such that information (such as a border) can be derived.

In some embodiments, the image interpretation application can apply one or more thresholds to generate a binary gradient mask at 320. That is, the gradient image can be calculated and a threshold can be applied to create a binary mask containing the segmented edges. In a more particular, the image interpretation application can use a Sobel operator or any other suitable operator to calculate the threshold value, where the threshold value is tuned and used to obtain a binary mask that contains the segmented edges.

It should be noted that, in some embodiments, the binary gradient mask shown in window 325 provides lines of high contrast in the image. However, the lines in the binary gradient mask may not delineate the outline of the object of interest. For example, due to the abundance of noise in the ultrasound image and/or other technical or acoustic difficulties, multiple short lines and unconnected targeted edge lines (e.g., gaps) were obtained within the binary gradient mask 325. Accordingly, at 330, the image interpretation application can dilate the binary gradient mask using linear structuring elements to enhance the connectivity of the edge lines in the horizontal direction. An example of a dilated gradient mask using linear structuring elements is shown in window 335.

In some embodiments, the image interpretation application can remove at least a portion of the features (e.g., lines with small pixel sizes) from the dilated binary gradient mask to form an updated binary image. In a more particular example, a connect component approach can be applied to the dilated gradient mask shown in window 345 to extract features with small pixel sizes. An example of the updated binary image with extracted features is shown in window 345.

Figure 4:
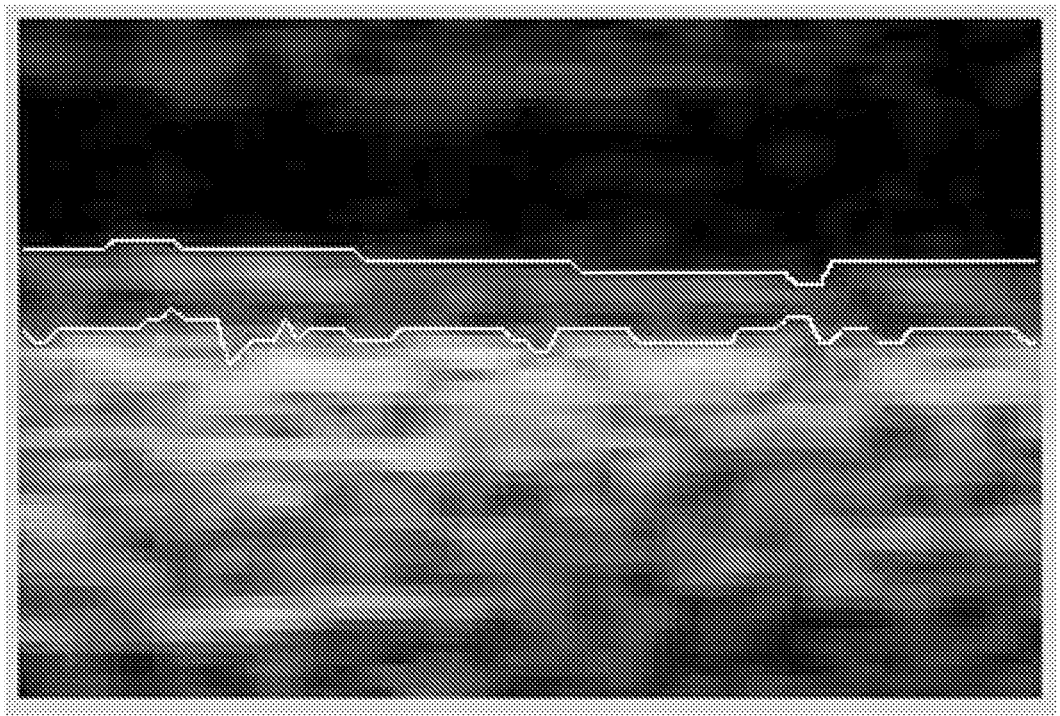
FIG. 4 is an illustrative display showing the detection of rough edges of the carotid artery in accordance with some embodiments of the disclosed subject matter.

Using the updated binary image, the image interpretation application can determine a first border at 350 and, based on the first detected border, the image interpretation can determine a second border at 360. In a more particular example, the upper border of the carotid lumen-intima interface can be designed as the first edge line while scanning from the top of the updated binary image. An example of the detected upper border of the carotid lumen-intima interface is shown in window 355. The lower border of the carotid media-adventitia interface can then be detected based on the detected upper border of the carotid lumen-intima interface. In some embodiments, to obtain the preliminary lower edge border of the carotid media-adventitia interface, the image interpretation application can scan from the detected upper border edge and down each column of pixels to obtain the pixel having the smallest value in gradient image. An illustrative example of the preliminary edge detection performed by the image interpretation application is shown in FIG. 4. As shown, the image interpretation application has detected the border of the carotid lumen-intima interface and a border of the carotid media-adventitia interface.

Referring back to FIG. 1, upon performing an initialization that detects the upper and lower preliminary edge lines, the image interpretation application can apply one or more active contour models to smoothen out the detected edge lines at 160. More particularly, the preliminary edges detected by the image interpretation application are used as the initial contours for the active contour model.

An active contour model (sometimes referred to herein as a "snake" or a "snake model") is a controlled continuity spline under the influence of internal forces and external forces. The position of a snake can be represented by:

$$v(s)=(s(s),y(s))$$

The energy function of the snake can then be represented by:

$$E_{snake}{}^* = \int_0^1 E_{snake}{}^*(v(s)ds) = \int_0^1 E_{int}(v(s)) + E_{ext}(v(s))ds$$

The first term in the energy function is the internal spline energy, which can be represented by:

$$\mathcal{T}(v) = \frac{1}{2}\int_0^L \alpha(s)\left|\frac{\partial v}{\partial s}\right|^2 + \beta(s)\left|\frac{\partial^2 v}{\partial s^2}\right|^2 ds$$

where α(s) controls the "tension" of the contour and β(s) regulates the "rigidity" of the contour. The second term in the energy function is an external image energy function, which can be represented as:

$$P(v)=\int_0^L P_1(v)ds$$

This can couple the snake to the image via a scalar potential function $P_1(v)$, which is generally calculated from l(x,y) through image processing. The Euler-Lagrange equations of motion for a dynamic snake can then be defined as:

$$\mu\frac{\partial^2 v}{\partial t^2} + \gamma\frac{\partial v}{\partial t} - \frac{\partial}{\partial s}\left(\alpha\frac{\partial v}{\partial s}\right) + \frac{\partial^2}{\partial s^2}\left(\frac{\partial^2 v}{\partial s^2}\right) = q(v)$$

It should be noted that the first two terms in the above-mentioned equation represent inertial forces due to the mass density, μ(s), and damping forces due to the dissipation density, γ(s), respectively. The following two terms in the above-mentioned equation represent the internal stretching and bending deformation forces. The right hand side of the above-mentioned equation includes the external forces, where $q(v)=-\nabla P_1(v)+f(s, t)$. The image forces are the negative gradient of the image potential function.

In some embodiments, the image interpretation application can allow the user to guide the dynamic snake via time-varying interaction forces, f(s,t). These forces can be applied to the snake through a user input device, such as a mouse, thereby driving the snake out of one energy minimizing equilibrium and into another.

In some embodiments, the image interpretation application can divide the snake contour into multiple snake elements. More particularly, the parametric domain can be partitioned into finite subdomains. Each element, e, can be represented geometrically using shape functions N(s) and nodal variables $u^e(t)$. The nodal variables of the elements are assembled into the snake nodal variable vector u(t). This leads to a discrete form of the equations of motion for a dynamic snake as a system of second-order ordinary differential equations in u(t):

$$M\ddot{u}+C\dot{u}+Ku=g$$

where M is the mass matrix, C is the damping matrix, K is the stiffness matrix, and g is the external force vector, which are assembled from corresponding element sub-matrices that depend on the shape functions N.

Accordingly, the image interpretation application can apply an active contour model to obtain smoothed edges or borders of the carotid artery. The active contour model causes the preliminary detected edge lines to be smooth and adherent to the gradient value of the region of interest.

Figure 5:
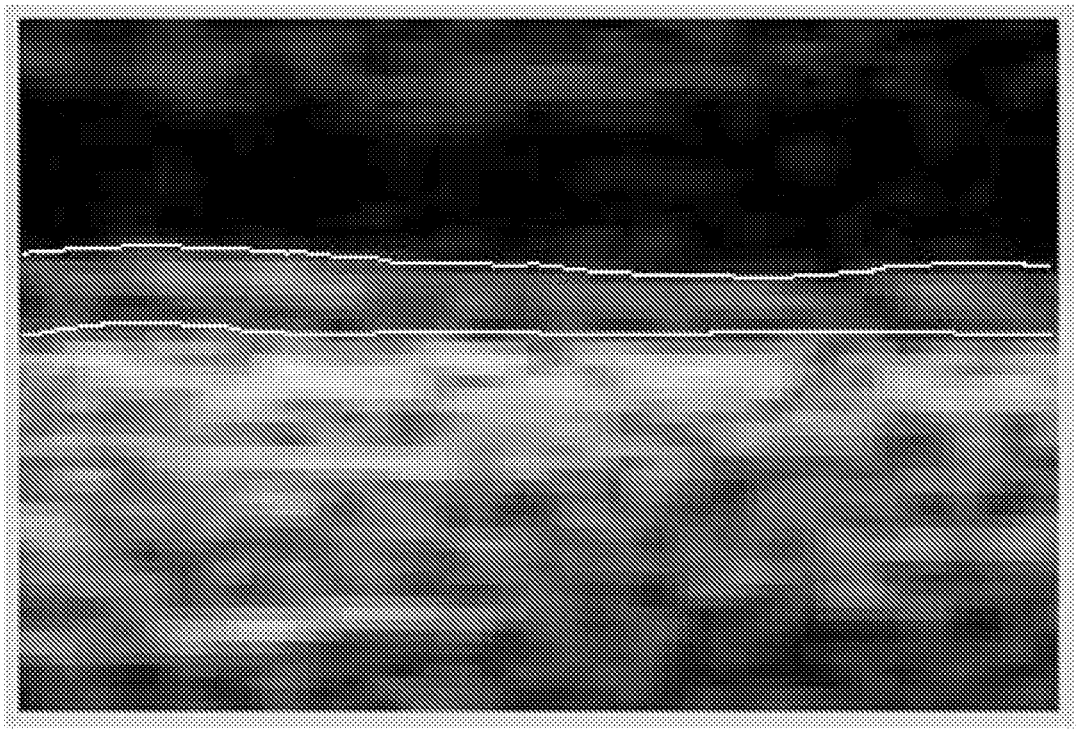
FIG. 5 is an illustrative display showing the detection of smooth edges of the carotid artery with the application of active contour models in accordance with some embodiments of the disclosed subject matter.

For example, while FIG. 4 illustrates the initialization approach where the image interpretation application detects preliminary edges, FIG. 5 illustrates the smoothed edge lines that result after applying one or more active contour models to the preliminary edge lines of FIG. 4.

Figure 7:
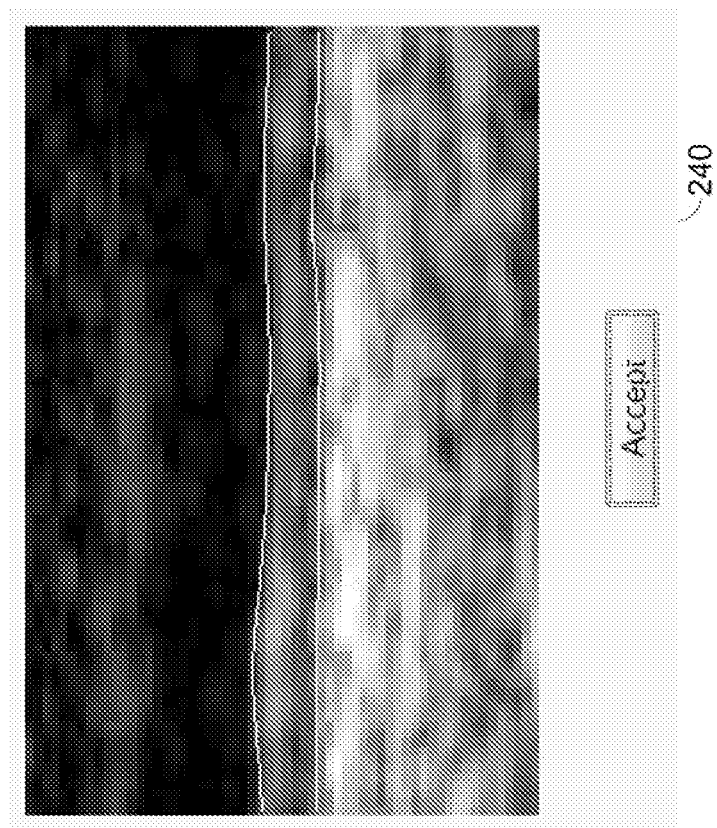
FIG. 7 is an enlarged version of the window showing the detected edges of the carotid artery shown in FIG. 2.
Figure 6:
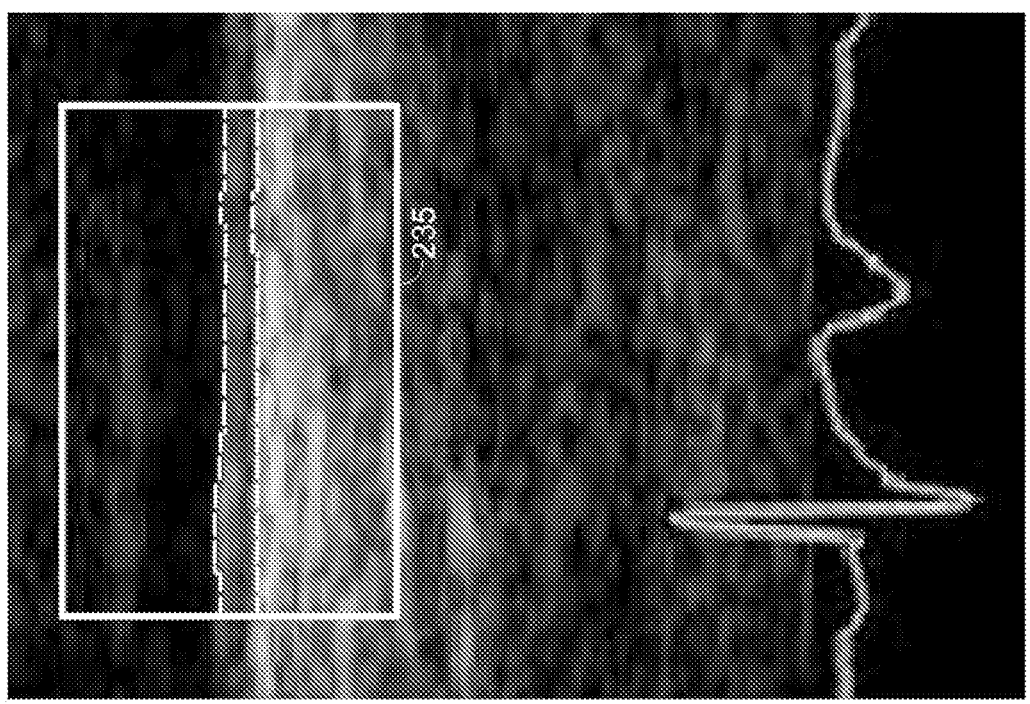
FIG. 6 is an enlarged version of the region of interest shown in FIG. 2.

In another example, the display screen 200 of FIG. 2 illustrates that, upon setting a region of interest, the image interpretation application obtains smooth edge lines of the carotid artery. More particularly, the upper border of the lumen-intima interface and the lower border of the media-adventitia interface are detected and shown within region of interest 235 and enlarged in window 250. These portions of FIG. 2 have been enlarged and are shown in FIGS. 6 and 7, respectively.

In some embodiments, the image interpretation application can provide the user with the opportunity to modify a smoothed edge line. For example, upon the user determining that the edge line detected from the border edge detection is not satisfactory (e.g., due to noise in the image or an image artifact, based on experience or judgment, etc.), the image interpretation application can allow the user to adjust the edge line.

Figure 8:
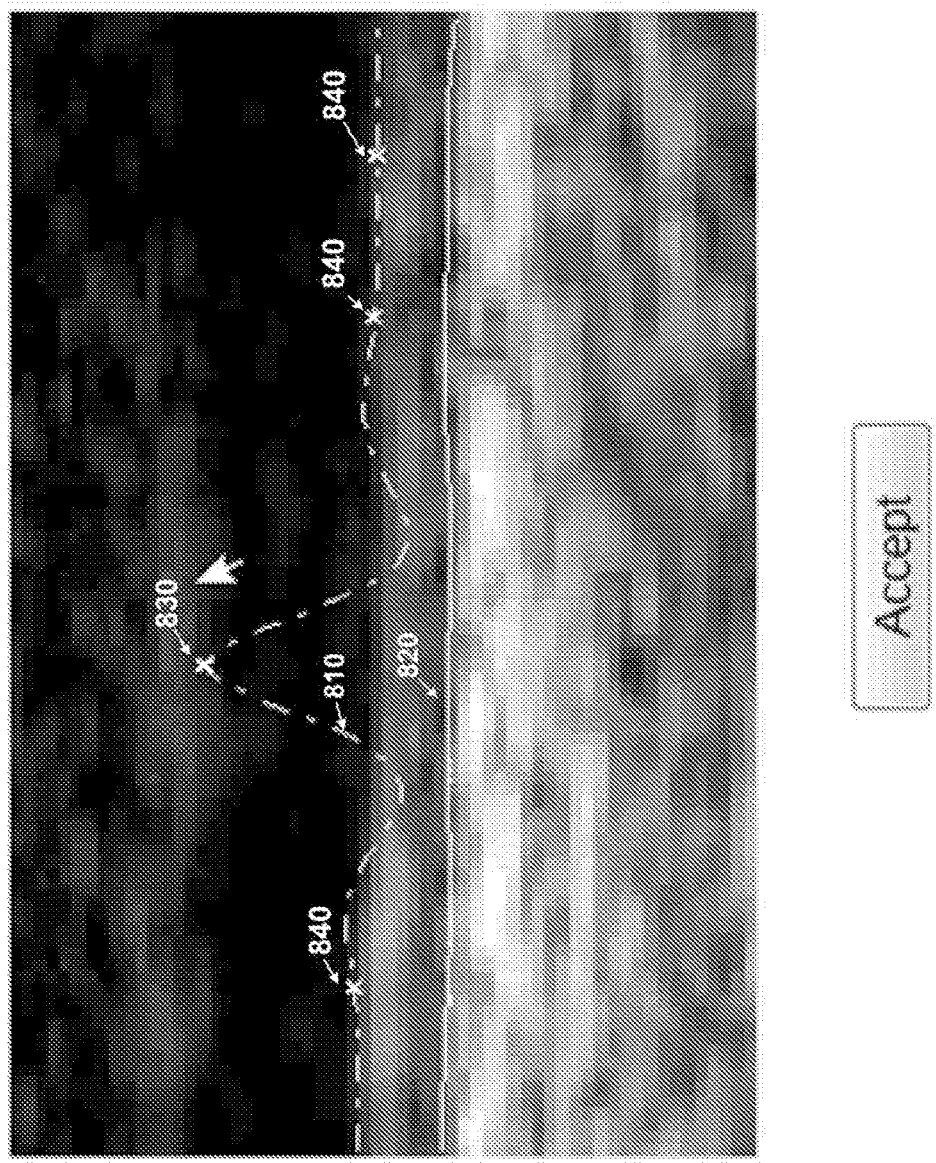
FIG. 8 is an illustrative display screen for receiving user input of constraints along a detected edge line in accordance with some embodiments of the disclosed subject matter.

In some embodiments, the image interpretation application can allow the user to modify a smoothed edge line with constraints or control points. In a more particular example, FIG. 8 shows an illustrative display screen for modifying the detected edge lines of the carotid artery. As shown, the image interpretation application has detected a first edge line 810 and a second edge line 820 of the carotid artery. As also shown, the image interpretation application provides the user with the opportunity to set hard constraints or control points for an edge line such that the edge line is directed to pass through the indicated control points (e.g., control points 830 and 840). More particularly, while calculating and displaying the edge line, the placement of hard constraints 830 and 840 causes the image interpretation application and its active contour model to provide an edge line that passes the user-positioned constraints or control points.

It should also be noted that, in some embodiments, the image interpretation application can update the edge line using the active contour model as the user moves a hard constraint. For example, as shown in FIG. 8, the user using a user input device can drag hard constraint 830 causing the image interpretation application to update the edge line with the current position of moveable hard constraint 830 and fixed hard constraints 840. It should be noted that the image interpretation application can allow the user to remove hard constraints, add any suitable number of hard constraints, etc.

It should further be noted that, in some embodiments, the image interpretation application can place hard constraints at the ends of the edge lines to inhibit them from shrinking or expanding in the horizontal direction.

It should be noted that constraints and/or other suitable modifications to the edge lines can be provided by mouse interaction or any other suitable interaction using a user input device. In a more particular example, when the image interpretation application is executed on a wireless communications device with a touch screen, the user may make contact with the touch screen using any suitable object or appendage, such as a stylus, finger, etc. For example, instead of moving a cursor over a point on an edge line, the image interpretation application may respond to contact with a touch screen, such as one or more taps on the touch screen, maintaining continuous contact with the touch screen, movement of the point of contact while maintaining continuous contact, a breaking of the contact, or any combination thereof.

For example, in some embodiments, the image interpretation application can allow a user to insert control points on an edge line with the use of a user input device. As shown in FIG. 8, the image interpretation application allows the user to click on a portion of edge line 810. In response to selecting a point on edge line 810, the image interpretation application can create control point 830. When the user maintains contact with control point 830 (e.g., by holding the mouse button down, by maintaining continuous contact with a touch screen, etc.), the image interpretation application can allow the user to move control point 830 to a different location, where one or more active contour models are used to update the edge line to pass through control point 830 at its current position and other control points 840.

In another example, the image interpretation application can allow a user to remove control points from an edge line. As shown in FIG. 8, in response to the user selecting an inserted control point (e.g., one of control points 830 or 840), the image interpretation application can provide the user with the option to remove the inserted control point. In response to removing an inserted control point, the image interpretation application can use one or more active contour models to update the edge line to pass through the remaining control points.

In yet another example, the image interpretation application can allow a user to correct or modify control points from an edge line. As shown in FIG. 8, in response to the user selecting an inserted control point (e.g., one of control points 830 or 840), the image interpretation application can provide the user with the option to modify the position of the inserted control point. In response to moving an inserted control point to another location, the image interpretation application can use one or more active contour models to update the edge line to pass through the control points, which includes the inserted control point at its new location.

Alternatively or additionally, the image interpretation application can allow a user to set particular designations for particular control points. For example, using a user input device, the image interpretation application can allow the user to designate that control point 830 is a measurement point for determining the carotid intima-media thickness. In response, the image interpretation application can determine the orthogonal distance from control point 830 on one edge line to the opposing edge line and present the measurement to the user.

Referring back to FIG. 1, the image interpretation application can then determine one or more measurements relating to the carotid artery using the detected edge lines at 180. For example, the image interpretation application can determine a mean intima-media thickness value. In a more particular example, the image interpretation application can determine the length of a line orthogonal from the detected media-adventitia border to the detected lumen-intima border for each of the points along the length of the region of interest within the carotid artery. The mean carotid intima-media thickness value can be the arithmetic mean value of these determined lengths. In another example, the image interpretation application can determine the maximum value of these lengths to derive the maximum carotid intima-media thickness value. In yet another example, the image interpretation application can determine a mean of the maximum carotid intima-media thickness values.

In some embodiments, the image interpretation application can determine a vascular age of the carotid artery in the selected ultrasound image. In particular, the image interpretation application can transmit a query to a storage device (e.g., a database that relates age to carotid intima-media thickness values in a particular study population). In response to transmitting the query, the image interpretation application can receive the associated vascular age and cause the vascular age to be displayed to the user. For example, as shown in region 240 of FIG. 2, the image interpretation application has queries a population database and determined that the vascular age of the carotid artery shown in window 230 is 43.62 years of age. In a more particular example, the image interpretation application accesses the median value (50th percentile) in a Bogalusa study database of a given race and gender.

It should be understood that the above steps of the flow diagrams of FIGS. 1 and 3 may be executed or performed in any order or sequence not limited to the order and sequence shown and described in the figure. Also, some of the above steps of the flow diagrams of FIGS. 1 and 3 may be executed or performed substantially simultaneously where appropriate or in parallel to reduce latency and processing times.

Figure 9:
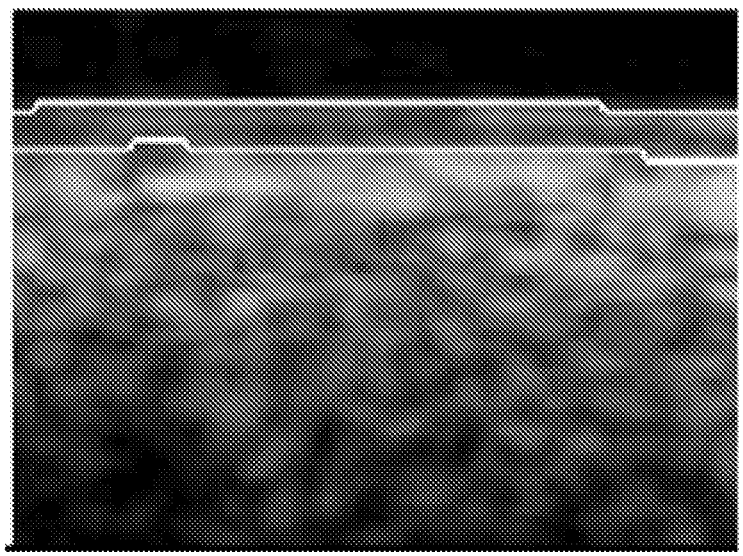
FIG. 9 shows the detection of the lumen-intima interface (the upper border) and the media-adventitia interface (lower border) using other detection approaches.
Figure 10:
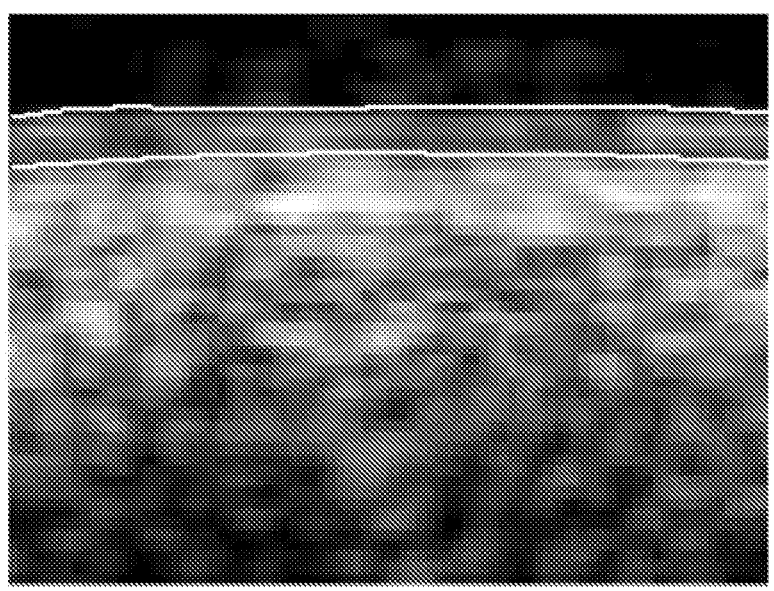
FIG. 10 shows the detection of the lumen-intima interface (the upper border) and the media-adventitia interface (lower border) in accordance with some embodiments of the disclosed subject matter.

FIGS. 9 and 10 show an illustrative comparison of the detection of the borders of a carotid artery using other detection approaches with the detection of the borders of the carotid artery of the same patient using the image interpretation application in accordance with some embodiments of the disclosed subject matter. As shown, the borders or edge lines detected by the image interpretation application provide a more accurate fit of the lumen-intima interface and the media-adventitia interface of the carotid artery.

In some embodiments, the image interpretation application can provide the user with various color indicators corresponding to carotid intima-media thickness and/or edge lines. For example, color indicators can overlay particular portions of the illustrative displays (e.g., over an edge line, over sections of an artery, over particular measurements, etc.) or otherwise displayed to provide the user with a visual recognition of particular conditions. More particularly, using the control indicators, the image interpretation application can provide the user with a visual indication of the range of thicknesses along a carotid artery—e.g., the region of the carotid artery with the maximum carotid intima-media thickness, the region of the carotid artery with the minimum carotid intima-media thickness, etc. In addition, the image interpretation application can provide the user with visual color cues for particular conditions, such as blue to indicate a thin intima media-thickness and red to indicate a thick intima-media thickness.

Figure 11:
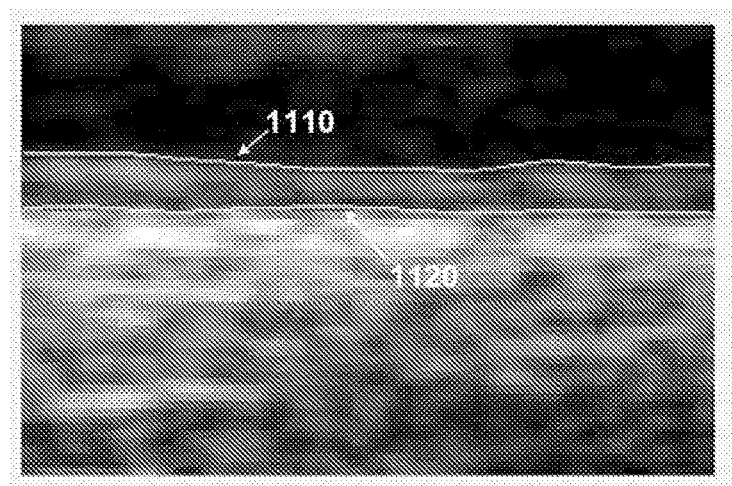
FIG. 11 is an illustrative display showing the detection of smooth edges of the carotid artery in accordance with some embodiments of the disclosed subject matter.

In a more particular embodiment, FIG. 11 shows two edge lines that have been detected using the image interpretation application. The image interpretation application can use color cues to indicate the detection of particular edge lines. For example, the detection of the lumen-intima interface can be shown by a green line 1110 and the detection of the media-adventitia interface can be shown by a red line 1120. It should be noted that any suitable color can be used such that the user is provided with a visual indication of the detected interfaces.

Figure 12:
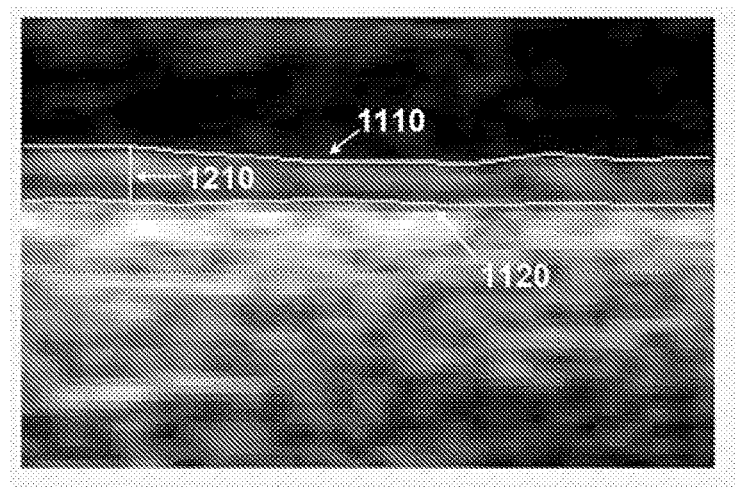
FIG. 12 is an illustrative display showing the display of FIG. 11 with an indicator that corresponds to the maximum carotid intima-media thickness in accordance with some embodiments of the disclosed subject matter.

In another more particular embodiment, FIG. 12 includes a measurement line 1210. The image interpretation application can display measurement line 1210 in yellow to indicate the orthogonal line that provides the maximum carotid intima-media thickness within the region of interest.

In some embodiments, the image interpretation application can allow the user to move measurement line 1210. For example, using the arrow keys on a keyboard or a finger on a touch screen, the image interpretation application can allow the user to move measurement line 1210 to another position within the region of interest. In response, the image interpretation application can provide the user with the carotid intima-media thickness value corresponding to the position of measurement line 1210. In another example, multiple measurement lines can be provided on the illustrative display—e.g., one measurement line corresponding to the location having the maximum carotid intima-media thickness, one measurement line corresponding to the location having the minimum carotid intima-media thickness, and/or one movable measurement line providing the carotid intima-media thickness value corresponding to its position.

Figure 13:
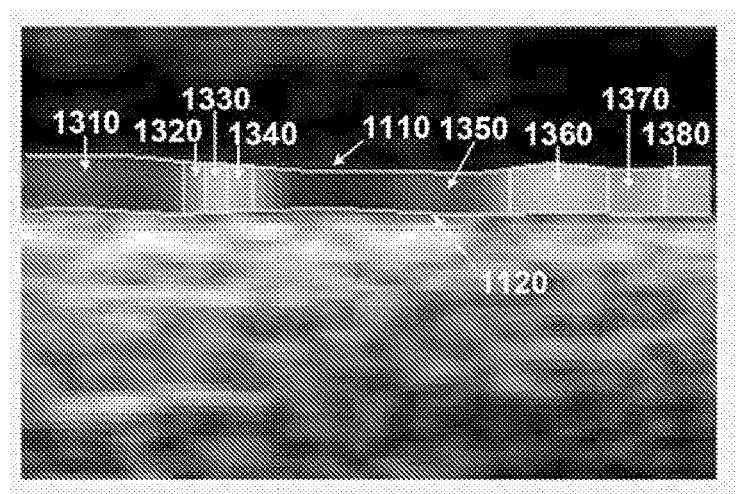
FIG. 13 is an illustrative display showing the display of FIG. 11 with color indicators that indicate the varying carotid intima-media thickness along the carotid artery in accordance with some embodiments of the disclosed subject matter.

In yet another more particular embodiment. FIG. 13 shows an illustrative example of a color-coded scheme or color indicators along the carotid artery. For example, the carotid artery within the region of interest can be divided into sections 1310, 1320, 1330, 1340, 1350, 1360, 1370, and 1380, where each section is assigned a color or shading based on the carotid intima-media thickness value or vascular age value (e.g., blue to indicate that the section of the carotid artery is within a normal carotid intima-media thickness range and red to indicate that the section of the carotid artery is within a significantly abnormal carotid intima-media thickness range). In another example, gradient shading or heat mapping can be used to show that the carotid intima-media thickness of section 1310 is significantly thicker than the carotid intima-media thickness of section 1350. In yet another example, gradient shading or heat mapping can be used to show changes in carotid intima-media thickness, where the red color assigned to section 1310 (to indicate a thick carotid intima-media thickness) transitions to the orange color assigned to neighboring section 1320. This can indicate the change in thickness and the direction of the change in thickness (e.g., that the carotid intima-media thickness decreases from section 1310 to section 1320).

In some embodiments, the image interpretation application can provide a color range indicator. For example, along with the color-coded sections of the carotid artery, the image interpretation application can display a color range indicator that provides a guide as to which sections are in a particular range of carotid intima-media thicknesses. In another example, the image interpretation application can display a color range indicator that indicates which portions of the carotid artery are within a normal carotid intima-media thickness range (blue), a moderately abnormal carotid intima-media thickness range (green), and a significantly abnormal carotid intima-media thickness range (red).

It should be noted that, although the embodiments described herein generally relate to measuring carotid intima-media thickness and vascular age, the image interpretation application can be used for any suitable measurements.

For example, instead of receiving ultrasound images from an ultrasound imaging device, the image interpretation application can receive x-ray computed tomography images. In a more particular example, upon receiving x-ray computed tomography images of a patient's spine, the image interpretation application can analyze the images and calculate spinal disc measurements, such as the distance between particular discs and the amount a particular disc is compressed. In another more particular example, upon receiving x-ray images of a patient, the image interpretation application can detect the borders of a bone and calculate measurements based on the detected borders, such as the length of a bone, the amount of displacement, In another example, the image interpretation application can receive fetal ultrasound images of a fetus, where the image interpretation application detects edge lines corresponding to the fetus and calculates measurements based on the detected edge lines, such as the length of the fetus, size of the baby's head, etc.

In yet another example, the image interpretation application can determine the carotid-intima media thickness of a patient's carotid artery and, in response to determining that the patient has atherosclerosis, the image interpretation application can transmit a message to a doctor.

In a further example, it should be noted that the image interpretation application can detect borders and perform various measurements using an ultrasound imaging device on any suitable artery, such as the brachial, radial, and/or femoral arteries.

Figure 14:
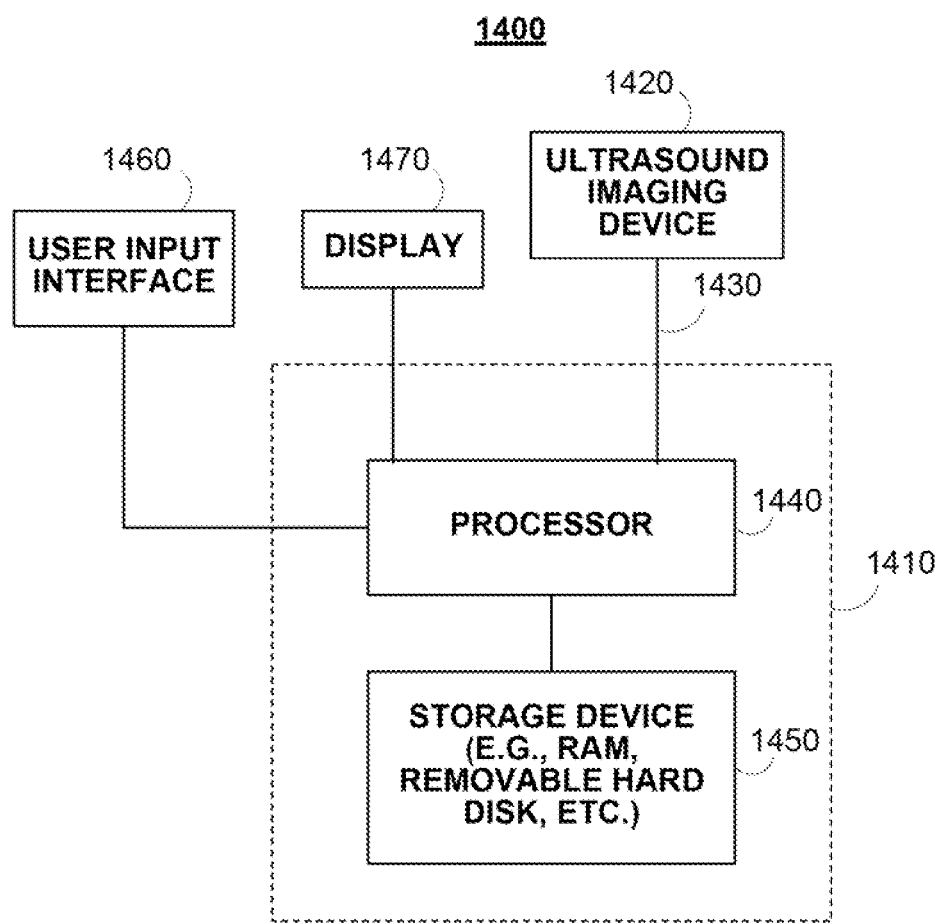
FIG. 14 shows an illustrative system for implementing the image interpretation application in accordance with some embodiments of the disclosed subject matter.

Turning to FIG. 14, FIG. 14 shows a generalized embodiment of an illustrative system 1400 on which the image interpretation application can be implemented in accordance with some embodiments of the disclosed subject matter. As shown, the illustrative system 1400 includes a computing device 1410 and an ultrasound imaging device 1420. Computing device 1410 can be any suitable computing device for providing access to the image interpretation application, such as a processor, a computer, a data processing device, or a combination of such devices. For example, the image interpretation application can be distributed into multiple backend components and multiple frontend components or interfaces. In a more particular example, backend components, such as data collection and data distribution can be performed on ultrasound imaging device 1420. Similarly, the graphical user interfaces displayed by the application, such as an interface for displaying ultrasound images and measuring carotid intima-media thickness, can be distributed by one or more computing devices 1410.

Ultrasound imaging device 1420 can be any suitable imaging device, such as a high resolution B-mode ultrasound imaging device with an 8-14 MHz linear array transducer utilizing fundamental frequency. Alternatively or additionally, any suitable imaging device (e.g., x-ray imaging device, magnetic resonance imaging device, etc.) can be connected to the computing device 1410 that is executing the image interpretation application.

More particularly, for example, computing device 1410 can be any of a general purpose device such as a computer or a special purpose device such as a client, a server, etc. Any of these general or special purpose devices can include any suitable components such as a processor (which can be a microprocessor, digital signal processor, a controller, etc.), memory, communication interfaces, display controllers, input devices, etc. For example, client 1410 can be implemented as a personal computer, a tablet computing device, a personal data assistant (PDA), a portable email device, a multimedia terminal, a mobile telephone, a gaming device, a set-top box, a television, etc.

In some embodiments, any suitable computer readable media can be used for storing instructions for performing the processes described herein, can be used to determine carotid intima-media thickness, etc. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Referring back to FIG. 14, communications link 1430 (and other links described herein) may be any communications links suitable for communicating data between computing device 1410 and ultrasound imaging device 1420, such as network links, dial-up links, wireless links, hard-wired links, any other suitable communications links, or a combination of such links. Computing device 1410 enables a user to access features of the image interpretation application. Computing device 1410 may be personal computers, laptop computers, mainframe computers, dumb terminals, data displays, Internet browsers, personal digital assistants ("PDAs"), two-way pagers, wireless terminals, portable telephones, any other suitable access device, or any combination of such devices. Computing device 1410 and ultrasound imaging device 1420 may be located at any suitable location. In one embodiment, computing device 1410 and ultrasound imaging device 1420 may be located within an organization. Alternatively, computing device 1410 and ultrasound imaging device 1420 may be distributed between multiple organizations.

It should also be noted that computing device 1410 can include processor 1440, memory 1450, input device 1460, and display 1470, which may be interconnected. In some embodiments, memory 1450 contains a storage device for storing a computer program for controlling processor 1440.

Processor 1440 uses the computer program to present on display 1470 the image interpretation application and the data received through communications link 1430 and commands and values transmitted by a user of computing device 1410. It should also be noted that data received through communications link 1430 or any other communications links may be received from any suitable source. Input device 1460 may be a computer keyboard, a mouse, a cursor-controller, dial, switchbank, lever, or any other suitable input device as would be used by a designer of input systems or process control systems. Alternatively, input device 1460 may be a finger or stylus used on a touch screen display 1470.

In some embodiments, the image interpretation application may include an application program interface (not shown), or alternatively, the application may be resident in the memory of computing device 1410. In another suitable embodiment, the only distribution to computing device 1410 may be a graphical user interface ("GUI") which allows a user to interact with the image interpretation application resident at, for example, another computing device.

In one particular embodiment, the image interpretation application may include client-side software, hardware, or both. For example, the application may encompass one or more Web-pages or Web-page portions (e.g., via any suitable encoding, such as HyperText Markup Language ("HTML"), Dynamic HyperText Markup Language ("DHTML"), Extensible Markup Language ("XML"), JavaServer Pages ("JSP"), Active Server Pages ("ASP"), Cold Fusion, or any other suitable approaches).

Accordingly, methods, systems, and media for determining carotid intima-media thickness are provided.

Although the invention has been described and illustrated in the foregoing illustrative embodiments, it is understood that the present disclosure has been made only by way of example, and that numerous changes in the details of implementation of the invention can be made without departing from the spirit and scope of the invention, which is only limited by the claims which follow. Features of the disclosed embodiments can be combined and rearranged in various ways.

What is claimed is:

1. A method for determining carotid intima-media thickness of a carotid artery, the method comprising:
    receiving a frame from a plurality of ultrasound images, wherein each of the plurality of ultrasound images includes a portion of the carotid artery, and the frame includes a plurality of pixels;
    receiving a user selection of a location within the frame;
    setting a region of interest based on the received user selection, wherein the region of interest defines a plurality of pixels within the region of interest;
    determining gradient values corresponding to the pixels within the region of interest based on intensity values for the pixels;
    comparing the gradient values to a threshold to determine binary values corresponding to the pixels within the region of interest, wherein the binary values form a plurality of high contrast lines within the region of interest;
    dilating the plurality of high contrast lines within the region of interest to form a plurality of dilated high contrast lines;
    detecting a first border within the region of interest by selecting a first dilated high contrast line from the plurality of dilated high contrast lines based on a position of the first dilated high contrast line relative to other of the plurality of dilated high contrast lines;
    detecting a second border within the region of interest by selecting a second dilated high contrast line from the plurality of dilated high contrast lines based on a position of the second dilated high contrast line relative to the first dilated high contrast line;
    applying one or more active contour models to the first border and the second border to generate a smoothed first border and a smoothed second border;
    calculating the intima-media thickness based at least in part on the smoothed first border and the second smoothed border; and
    displaying the frame and the intima-media thickness.

2. The method of claim 1, further comprising receiving a hard constraint on at least one of the smoothed first border and the smoothed second border, wherein the one or more active contour models are applied such that the smoothed first border or the smoothed second border are directed through the hard constraint.

3. The method of claim 2, further comprising automatically updating the smoothed first border or the second smoothed border in response to modifying the hard constraint.

4. The method of claim 2, further comprising automatically updating the smoothed first border or the second smoothed border using the one or more active contour models in response to receiving a plurality of hard constraints.

5. The method of claim 1, wherein the smoothed first border is a lumen-intima interface of the carotid artery and the smoothed second border is a media-adventitia interface of the carotid artery.

6. The method of claim 1, wherein the region of interest includes a plurality of horizontal pixels, wherein calculating the intima-media thickness further comprises determining a plurality of carotid intima-media length values, and wherein each of the plurality of carotid intima-media length values is a length of a line orthogonal from the smoothed first border to the smoothed second border for each horizontal pixel within the region of interest.

7. The method of claim 6, further comprising determining at least one of: a mean carotid intima-media thickness from the plurality of carotid intima-media length values, a maximum carotid intima-media thickness from the plurality of carotid intima-media length values, and a mean of the maximum carotid intima-media thickness from the plurality of carotid intima-media length values over a plurality of regions of interest along the carotid artery.

8. The method of claim 1, further comprising:
    transmitting the carotid intima-media thickness to a database that relates age to carotid intima-media thickness values; and
    receiving a vascular age corresponding to the carotid artery from the database.

9. The method of claim 1, further comprising:
    initializing the one or more active contour models by automatically detecting a first rough border and a second rough border within the region of interest; and
    providing the first rough border and the second rough border to the one or more active contour models.

10. The method of claim 1, further comprising simultaneously displaying the first smoothed border, the second smoothed border, and an orthogonal line connecting the first smoothed border and the second smoothed border identifying a location of a maximum carotid intima-media thickness, wherein a color indicator is assigned to each of the first smoothed border and the second smoothed border to indicate the detected borders.

11. The method of claim 1, further comprising assigning a color indicator to a portion of the carotid artery within the region of interest to indicate a range of the carotid intima-media thickness for the portion.

12. A system for determining carotid intima-media thickness of a carotid artery, the system comprising:
    a memory; and
    a hardware processor coupled to the memory and configured to:
        receive a frame from a plurality of ultrasound images, wherein each of the plurality of ultrasound images includes a portion of the carotid artery, and the frame includes a plurality of pixels;
        receive a user selection of a location within the frame;
        set a region of interest based on the received user selection, wherein the region of interest defines a plurality of pixels within the region of interest;
        determine gradient values corresponding to the pixels within the region of interest based on intensity values for the pixels;
        compare the gradient values to a threshold to determine binary values corresponding to the pixels within the region of interest, wherein the binary values form a plurality of high contrast lines within the region of interest;

dilate the plurality of high contrast lines within the region of interest to form a plurality of dilated high contrast lines;

detect a first border within the region of interest by selecting a first dilated high contrast line from the plurality of dilated high contrast lines based on a position of the first dilated high contrast line relative to other of the plurality of dilated high contrast lines;

detect a second border within the region of interest by selecting a second dilated high contrast line from the plurality of dilated high contrast lines based on a position of the second dilated high contrast line relative to the first dilated high contrast line;

apply one or more active contour models to the first border and the second border to generate a smoothed first border and a smoothed second border;

calculate the intima-media thickness based at least in part on the smoothed first border and the second smoothed border; and display the frame and the intima-media thickness.

13. The system of claim 12, wherein the hardware processor is further configured to receive a hard constraint on at least one of the smoothed first border and the smoothed second border, wherein the one or more active contour models are applied such that the smoothed first border or the smoothed second border are directed through the hard constraint.

14. The system of claim 13, wherein the hardware processor is further configured to automatically update the smoothed first border or the second smoothed border in response to modifying the hard constraint.

15. The system of claim 13, wherein the hardware processor is further configured to automatically update the smoothed first border or the second smoothed border using the one or more active contour models in response to receiving a plurality of hard constraints.

16. The system of claim 12, wherein the smoothed first border is a lumen-intima interface of the carotid artery and the smoothed second border is a media-adventitia interface of the carotid artery.

17. The system of claim 12, wherein the region of interest includes a plurality of horizontal pixels, wherein calculating the intima-media thickness further comprises determining a plurality of carotid intima-media length values, and wherein each of the plurality of carotid intima-media length values is a length of a line orthogonal from the smoothed first border to the smoothed second border for each horizontal pixel within the region of interest.

18. The system of claim 17, wherein the hardware processor is further configured to determine at least one of: a mean carotid intima-media thickness from the plurality of carotid intima-media length values, a maximum carotid intima-media thickness from the plurality of carotid intima-media length values, and a mean of the maximum carotid intima-media thickness from the plurality of carotid intima-media length values over a plurality of regions of interest along the carotid artery.

19. The system of claim 12, wherein the hardware processor is further configured to:
transmit the carotid intima-media thickness to a database that relates age to carotid intima-media thickness values; and
receive a vascular age corresponding to the carotid artery from the database.

20. The system of claim 12, wherein the hardware processor is further configured to:

initialize the one or more active contour models by automatically detecting a first rough border and a second rough border within the region of interest; and
provide the first rough border and the second rough border to the one or more active contour models.

21. The system of claim 12, wherein the hardware processor is further configured to simultaneously display the first smoothed border, the second smoothed border, and an orthogonal line connecting the first smoothed border and the second smoothed border identifying a location of a maximum carotid intima-media thickness, wherein a color indicator is assigned to each of the first smoothed border and the second smoothed border to indicate the detected borders.

22. The system of claim 12, wherein the hardware processor is further configured to assign a color indicator to a portion of the carotid artery within the region of interest to indicate a range of the carotid intima-media thickness for the portion.

23. A non-transitory computer-readable medium containing computer-executable instructions that, when executed by a processor, cause the processor to perform a method for determining carotid intima-media thickness, the method comprising:
receiving a frame from a plurality of ultrasound images, wherein each of the plurality of ultrasound images includes a portion of the carotid artery, and the frame includes a plurality of pixels;
receiving a user selection of a location within the frame;
setting a region of interest based on the received user selection, wherein the region of interest defines a plurality of pixels within the region of interest;
determining gradient values corresponding to the pixels within the region of interest based on intensity values for the pixels;
comparing the gradient values to a threshold to determine binary values corresponding to the pixels within the region of interest, wherein the binary values form a plurality of high contrast lines within the region of interest;
dilating the plurality of high contrast lines within the region of interest to form a plurality of dilated high contrast lines;
detecting a first border within the region of interest by selecting a first dilated high contrast line from the plurality of dilated high contrast lines based on a position of the first dilated high contrast line relative to other of the plurality of dilated high contrast lines;
detecting a second border within the region of interest by selecting a second dilated high contrast line from the plurality of dilated high contrast lines based on a position of the second dilated high contrast line relative to the first dilated high contrast line;
applying one or more active contour models to the first border and the second border to generate a smoothed first border and a smoothed second border;
calculating the intima-media thickness based at least in part on the smoothed first border and the second smoothed border; and
displaying the frame and the intima-media thickness.

24. The non-transitory computer-readable medium of claim 23, wherein the method further comprises receiving a hard constraint on at least one of the smoothed first border and the smoothed second border, wherein the one or more active contour models are applied such that the smoothed first border or the smoothed second border are directed through the hard constraint.

25. The non-transitory computer-readable medium of claim 24, wherein the method further comprises automatically updating the smoothed first border or the second smoothed border in response to modifying the hard constraint.

26. The non-transitory computer-readable medium of claim 24, wherein the method further comprises automatically updating the smoothed first border or the second smoothed border using the one or more active contour models in response to receiving a plurality of hard constraints.

27. The non-transitory computer-readable medium of claim 23, wherein the smoothed first border is a lumen-intima interface of the carotid artery and the smoothed second border is a media-adventitia interface of the carotid artery.

28. The non-transitory computer-readable medium of claim 23, wherein the region of interest includes a plurality of horizontal pixels, wherein calculating the intima-media thickness further comprises determining a plurality of carotid intima-media length values, and wherein each of the plurality of carotid intima-media length values is a length of a line orthogonal from the smoothed first border to the smoothed second border for each horizontal pixel within the region of interest.

29. The non-transitory computer-readable medium of claim 28, wherein the method further comprises determining at least one of: a mean carotid intima-media thickness from the plurality of carotid intima-media length values, a maximum carotid intima-media thickness from the plurality of carotid intima-media length values, and a mean of the maximum carotid intima-media thickness from the plurality of carotid intima-media length values over a plurality of regions of interest along the carotid artery.

30. The non-transitory computer-readable medium of claim 23, wherein the method further comprises:
transmitting the carotid intima-media thickness to a database that relates age to carotid intima-media thickness values; and
receiving a vascular age corresponding to the carotid artery from the database.

31. The non-transitory computer-readable medium of claim 23, wherein the method further comprises:
initializing the one or more active contour models by automatically detecting a first rough border and a second rough border within the region of interest; and
providing the first rough border and the second rough border to the one or more active contour models.

32. The non-transitory computer-readable medium of claim 23, wherein the method further comprises simultaneously displaying the first smoothed border, the second smoothed border, and an orthogonal line connecting the first smoothed border and the second smoothed border identifying a location of a maximum carotid intima-media thickness, wherein a color indicator is assigned to each of the first smoothed border and the second smoothed border to indicate the detected borders.

33. The non-transitory computer-readable medium of claim 23, wherein the method further comprises assigning a color indicator to a portion of the carotid artery within the region of interest to indicate a range of the carotid intima-media thickness for the portion.

* * * * *